(12) United States Patent
Carmeliet et al.

(10) Patent No.: US 7,858,593 B2
(45) Date of Patent: Dec. 28, 2010

(54) INHIBITORS OF PROLYL-HYDROXYLASE-1 FOR THE TREATMENT OF SKELETAL MUSCLE DEGENERATION

(75) Inventors: Peter Carmeliet, Blanden (BE); Julián Aragonés López, Madrid (ES)

(73) Assignees: VIB VZW, Ghent (BE); Life Sciences Research Partners VZW, Leuven (BE)

( * ) Notice: Subject to any disclaimer, the term of this patent is extended or adjusted under 35 U.S.C. 154(b) by 10 days.

(21) Appl. No.: 12/218,174

(22) Filed: Jul. 11, 2008

(65) Prior Publication Data

US 2009/0047294 A1 Feb. 19, 2009

Related U.S. Application Data

(63) Continuation of application No. PCT/EP2007/050452, filed on Jan. 17, 2007.

(30) Foreign Application Priority Data

Jan. 17, 2006 (EP) .................................. 06100440

(51) Int. Cl.
  *A01N 43/04* (2006.01)
  *A61K 31/70* (2006.01)
(52) U.S. Cl. ........................................................ 514/44
(58) Field of Classification Search .................... 514/44
  See application file for complete search history.

(56) References Cited

U.S. PATENT DOCUMENTS

| 5,545,806 | A | 8/1996 | Lonberg et al. | |
|---|---|---|---|---|
| 2004/0146964 | A1 | 7/2004 | Maxwell et al. | |
| 2004/0204356 | A1 * | 10/2004 | Guenzler-Pukall et al. | .... 514/12 |
| 2004/0254215 | A1 | 12/2004 | Arend et al. | |
| 2005/0119243 | A1 * | 6/2005 | Harris et al. | ................. 514/184 |
| 2006/0216295 | A1 * | 9/2006 | Crabtree et al. | .......... 424/145.1 |

FOREIGN PATENT DOCUMENTS

| WO | WO 94/01131 | 1/1994 |
|---|---|---|
| WO | WO 94/04672 | 3/1994 |
| WO | WO 94/04678 | 3/1994 |
| WO | WO 94/25591 | 11/1994 |
| WO | WO 97/49805 | 12/1997 |
| WO | WO 99/14220 | 3/1999 |
| WO | WO 02/074981 | 9/2002 |

OTHER PUBLICATIONS

Mason et al. (PLOS Biology 2:1540-1548, 2004).*
Epstein et al., C. Elegans EGL-9 and Mammalian Homologs Define a Family of Dioxygenases that Regulate HIF by Prolyl Hydroxylation, Cell, Oct. 5, 2001, pp. 43-54, vol. 107, No. 1.
Appeloff et al., Differential function of the prolyl hydroxylases PHD1, PHD2, and PHD3 in the regulation of hypoxia-inducible factor, Journal of Biological Chemistry, Sep. 10, 2004, pp. 38458-38465, vol. 279, No. 37.
Takeda et al., Placental but not heart defects are associated with elevated hypoxia-inducible factor alpha levels in mice lacking prolyl hydroxylase domain protein 2, Molecular and Cellular Biology, Nov. 2006, pp. 8336-8346, vol. 26, No. 22.
Erez et al., Hypoxia-dependent regulation of PHD1: Cloning and Characterization of the human PHD1/EGLN2 gene promoter, FEBS Letters, Jun. 4, 2004, pp. 311-315, vol. 567, No. 2-3.
Bruick et al., A conserved family of prolyl-4-hydroxylases that modify HIF, Science, Nov. 9, 2001, pp. 1337-1340, vol. 294, No. 5545.
U.S. Appl. No. 12/459,463, filed Jul. 1, 2009, Inventor: Carmeliet et al., Title: Means and Methods for the Recruitment and Identification of Stem Cells.
U.S. Appl. No. 61/341,432, filed Mar. 30, 2010, Inventor: Mazzone et al., Title: Induction of Arteriogenesis by Cell Therapy With Polarized Myeloid Cells.
U.S. Appl. No. 12/658,284, filed Feb. 10, 2010, Inventor: Peter Carmeliet, Title: Treatment of Amyotrophic Lateral Sclerosis.

* cited by examiner

*Primary Examiner*—Brian Whiteman
(74) *Attorney, Agent, or Firm*—TraskBritt, P.C.

(57) ABSTRACT

The invention relates to the field of muscle pathologies, more particularly to the field of diseases where skeletal muscle degeneration occurs. The invention describes transgenic mice that do not produce prolyl-hydroxylase-1, -2 or -3. It is revealed that the phenotype of the prolyl-hydroxylase 1 knock-out mouse is characterized by a protection of skeletal muscle atrophy due to a variety of muscle damages, especially ischemic insults. The invention thus relates to the use of molecules that can bind to prolyl-hydroxylase-1 for the prevention and/or treatment of skeletal muscle degeneration.

6 Claims, 2 Drawing Sheets

INHIBITORS OF PROLYL-HYDROXYLASE-1 FOR THE TREATMENT OF SKELETAL MUSCLE DEGENERATION

CROSS REFERENCE TO RELATED APPLICATIONS

This application is a continuation of International Patent Application PCT/EP2007/050452 filed Jan. 17, 2007, and published, in English, as International Patent Publication WO 2007/082899 A1 on Jul. 26, 2007, which claims priority to European Patent Application Serial No. EP 06100440.4 filed Jan. 17, 2006, the entire contents of each of which are hereby incorporated herein by this reference.

TECHNICAL FIELD

The invention relates to the field of muscle pathologies and, more particularly, to the field of diseases where skeletal muscle degeneration occurs. Described are transgenic mice that do not produce prolyl-hydroxylase-1, -2 or -3. It is revealed that the phenotype of the prolyl-hydroxylase 1 knock-out mouse is characterized by a protection of skeletal muscle atrophy due to a variety of muscle damages, especially ischemic insults. The invention thus relates to the use of molecules that can bind to prolyl-hydroxylase-1 for the prevention and/or treatment of skeletal muscle degeneration.

BACKGROUND OF THE INVENTION

When challenged by hypoxia, cells increase the expression of proteins involved in the physiological adaptation to low oxygen environments. This compensatory response depends on the activation of heterodimeric transcription factors, designated hypoxia-inducible factors (HIF).[1-3] Three different HIF-alpha subunits (HIF-1α, HIF-2α or HIF-3α) and one beta-subunit (HIF-1β or Aryl Hydrocarbon Receptor Nuclear Translocator, ARNT), all belonging to the basic helix-loop-helix family, have been identified to date.[4-6] The beta-subunit is constitutively expressed, while the alpha-subunits are tightly regulated by oxygen levels.[7] In normoxia, interaction with the von Hippel-Lindau (VHL) tumor suppressor, a component of the E3 ubiquitin ligase complex, leads to ubiquitinization and subsequent proteasome-dependent degradation of HIF-1α subunits.[8-10] In hypoxia, however, HIF-1α subunits lose their ability to interact with VHL, and are subsequently stabilized.[7,11]

The nature of the oxygen sensors regulating the VHL-HIF-1α interaction and, therefore, HIF-1α-activity has long remained elusive. Recent evidence indicated that a prolyl hydroxylase (PH) enzyme is involved in oxygen sensing.[12,13] VHL interacts with two independent sites of the HIF-1α subunits containing specific proline residues. Hydroxylation of these proline residues, which is required for the interaction of VHL with HIF-1α,[14] is catalyzed by a novel family of mammalian proline hydroxylases named PHD1, PHD2 and PHD3, all belonging to the iron (II)-2-oxoglutarate-dependent dioxygenases family.[15,16] PHD-dependent hydroxylation of HIF-1α subunits requires oxygen. Thus, under hypoxic conditions, HIF-1α is not hydroxylated, and escapes VHL-dependent degradation. Consequently, HIF-1α subunits are enabled to translocate to the nucleus, where they associate with ARNT to form heterodimers that bind to the DNA-specific HRE (hypoxia response elements) of different target genes.[17] Knock-down of PHD-activity enhances the HIF-1α-dependent compensatory gene expression program in vitro,[18,19] and peptides containing the PHD prolyl hydroxylation sites act as competitive inhibitors of endogenous prolyl hydroxylation, causing HIF stabilization and increased vessel growth.[20,21]

Nonetheless, it remains to be determined to which extent the PHD enzymes have overlapping or unique tissue-specific activities in vivo, which molecules are downstream PHD targets, and whether specific prolyl hydroxylases could serve as potential drug targets to modulate tissue responses to oxygen deprivation. As hypoxia plays a significant role in ischemic cardiovascular disease, cancer, stroke, and chronic lung disease, understanding the role of each PHD enzyme is of critical importance. Prolyl hydroxylases and non-specific inhibitors have been described in US20040254215, Fibrogen Inc., and in US20040146964, Isis Innovation. As described herein, we report the inactivation of the PHD1, PHD2 and PHD3 locus, as well as inheritance and viability of mice lacking each single PHD. Absence of PHD2 results in embryonic lethality, precluding the analysis of its role in pathological conditions in adult mice.

DISCLOSURE OF THE INVENTION

The role of proline hydroxylase oxygen sensors in the tissue response to ischemia was analyzed in a model of acute hind limb ischemia in PHD1$^{-/-}$, PHD2$^{+/-}$ and PHD3$^{-/-}$ mice, which survived to adulthood. Our data surprisingly reveal that skeletal muscle injury, analyzed in the gastrocnemius muscle of ischemic hind limbs, is strikingly reduced only in PHD1$^{-/-}$ mice. Further in vivo inactivation studies, using hairpin interference RNA, show a benefit of therapeutic PHD1-targeting in pathological conditions leading to skeletal muscle damage and degeneration.

Continuous satisfaction of oxygen demands in tissues relies on the appropriate vascular perfusion as well as blood oxygen-carrying capacity. Oxygen delivery to tissues is continuously sensed by PHD1, PHD2 and PHD3 hydroxylases that use oxygen to keep HIF-dependent responses in silence when adequate oxygen levels reach tissues. The striking sensitivity of PHDs to oxygen make these prolyl hydroxylases derepress HIFs to conditions ranging from moderate to severe hypoxia.[23] A great interest has been raised to unravel the relative in vivo roles of each PHD oxygen sensor because tissue deprivation of oxygen (hypoxia) is common in cardiovascular diseases. Previous data revealed that PHD members shared a common biological function targeting HIF for degradation and specific functions for each isoform have not been identified.[15,19] As described herein, mice deficient for PHD1, PHD2 and PHD3, three recently identified oxygen sensors of mammalian tissues were generated. Homozygous PHD2 deficiency is embryonically lethal, but PHD1$^{-/-}$ and PHD3$^{-/-}$ mice are viable.

Interestingly, although PHD1, 2 and 3 are expressed in skeletal muscle, here it is reported that only PHD1$^{-/-}$ mice, in contrast to PHD2$^{+/-}$ and PHD3$^{-/-}$ mice, shows striking skeletal muscle protection after acute hind limb ischemia. PHD1$^{-/-}$ mice display a striking preservation of myofiber viability in acute hind limb ischemia, a condition leading to severe skeletal muscle necrosis in wild-type mice. This myoprotective effect is not attributable to an enhanced arteriogenic and angiogenic response. Glycolytic potential is increased in PHD1$^{-/-}$ muscles and, in ischemic conditions, cellular energy sources are sustained via a rapid compensatory shift from oxidative towards glycolytic energy metabolism. Although the analysis in PHD2$^{-/-}$ skeletal muscle is precluded by the fact that PHD2$^{-/-}$ succumb during embryonic development, our data define a specific role attributed to PHD1-dependent signaling in skeletal muscle preservation that cannot be promoted by PHD3 deficiency or PHD2 haplo insufficiency.

Furthermore, histological signs show that skeletal muscle protection starts as early as 24 hours of ischemia and is sustained precluding any skeletal damage after vascular occlusion. In this regard, PHD1$^{-/-}$ mice, in contrast to PHD1$^{+/+}$ mice, develop an alternative and extremely fast response to ischemia in 60 minutes that satisfies energy demands. Thus, described is the use of inhibitors of PHD-1 for the treatment of disorders involving diseases where skeletal muscle degeneration occurs, more particularly, to the treatment of diseases where skeletal muscle degeneration occurs due to ischemia.

The wording "diseased skeletal muscle cells" refers to skeletal muscle cells that have been exposed, for example, to an ischemic insult or, for example, skeletal muscle cells that possess a reduced glycolytic rate, or, for example, skeletal muscle cells that have been exposed to serum deprivation. Molecules that can be used are molecules that are able to neutralize the activity of PHD-1 by interfering with its synthesis, translation or proteolytical activity.

By "molecules" it is meant peptides, tetrameric peptides, proteins, organic molecules, antibodies, ribozymes, siRNAs, anti-sense nucleic acids and locked nucleic acids (LNAs). Also, the invention is directed to the use of antagonists of PHD-1, such as anti-PHD-1 antibodies and functional fragments derived thereof, anti-sense RNA and DNA molecules and ribozymes that function to inhibit the translation of PHD-1.

By "synthesis" it is meant transcription of PHD-1. Small molecules can bind on the promoter region of PHD-1 and inhibit binding of a transcription factor or the molecules can bind the transcription factor and inhibit binding to the PHD-1-promoter.

By "PHD-1" it is meant "prolyl hydroxylase-1" protein. The nucleotide sequence of human PHD-1 is depicted in SEQ ID NO:1 and the amino acid sequence of human PHD-1 is depicted in SEQ ID NO:2. The nucleotide sequence of mouse PHD-1 is depicted in SEQ ID NO:3 and the amino acid sequence of mouse PHD-1 is depicted in SEQ ID NO:4. The activity of PHD-1 can be calculated by measuring the % inhibition of degeneration of skeletal muscle cells. It is also clear that undifferentiated myoblast cultures can be used instead of skeletal muscle cells.

"Degeneration" is herein equivalent to the terms necrotic skeletal muscle cell death, apoptotic muscle skeletal cell death, muscle skeletal cell atrophy and skeletal fiber injury. Since PHD-1 also possesses a hydroxylation activity, its activity can also be calculated by measuring the hydroxylation of its substrates (e.g., HIF).

In a specific embodiment, the invention uses an antibody against PHD-1. The term "antibody" or "antibodies" relates to an antibody characterized as being specifically directed against PHD-1 or any functional derivative thereof, with the antibodies being preferably monoclonal antibodies; or an antigen-binding fragment thereof, of the F(ab')$_2$, F(ab) or single chain Fv type, or any type of recombinant antibody derived thereof. These antibodies of the invention, including specific polyclonal antisera prepared against PHD-1 or any functional derivative thereof, have no cross-reactivity to other proteins. The monoclonal antibodies of the invention can, for instance, be produced by any hybridoma liable to be formed according to classical methods from splenic cells of an animal, particularly of a mouse or rat immunized against PHD-1 or any functional derivative thereof, and of cells of a myeloma cell line, and to be selected by the ability of the hybridoma to produce the monoclonal antibodies recognizing PHD-1 or any functional derivative thereof that have been initially used for the immunization of the animals.

The monoclonal antibodies according to this embodiment may be humanized versions of the mouse monoclonal antibodies made by means of recombinant DNA technology, departing from the mouse and/or human genomic DNA sequences coding for H and L chains or from cDNA clones coding for H and L chains. Alternatively, the monoclonal antibodies according to this embodiment of the invention may be human monoclonal antibodies. Such human monoclonal antibodies are prepared, for instance, by means of human peripheral blood lymphocyte (PBL) repopulation of severe combined immune deficiency (SCID) mice as described in PCT/EP 99/03605 or by using transgenic non-human animals capable of producing human antibodies as described in U.S. Pat. No. 5,545,806.

Also, fragments derived from these monoclonal antibodies such as Fab, F(ab)'$_2$ and ssFv ("single chain variable fragment"), providing they have retained the original binding properties, form part of the invention. Such fragments are commonly generated by, for instance, enzymatic digestion of the antibodies with papain, pepsin, or other proteases. It is well known to the person skilled in the art that monoclonal antibodies, or fragments thereof, can be modified for various uses. The antibodies involved as described herein can be labeled by an appropriate label of the enzymatic, fluorescent, or radioactive type. In certain embodiments, antibodies against PHD-1 or a functional fragment thereof are derived from camels. Camel antibodies are fully described in WO94/25591, WO94/04678 and in WO97/49805. Processes are described in the art that make it possible that antibodies can be used to hit intracellular targets. Since PHD-1 is an intracellular target, the antibodies or fragments thereof with a specificity for PHD-1 must be delivered into the cells. One such technology uses lipidation of the antibodies. The latter method is fully described in WO 94/01131 and these methods are herein incorporated by reference.

Small molecules, e.g., small organic molecules, and other drug candidates can be obtained, for example, from combinatorial and natural product libraries. To screen for candidate/test molecules, skeletal muscle cell lines that express PHD-1 may be used and the loss of skeletal muscle cell degeneration can be monitored as described in detail in the examples. Monitoring can also be measured using standard biochemical techniques. Other responses, such as activation or suppression of catalytic activity, phosphorylation or dephosphorylation of other proteins, activation or modulation of second messenger production, measuring the hydroxylation activity of its substrates (e.g., HIF), measurement of the intracellular levels of energy-rich phosphates, measurement of the anaerobic energy metabolism, changes in cellular ion levels, association, dissociation or translocation of signaling molecules, or transcription or translation of specific genes, may also be monitored. These assays may be performed using conventional techniques developed for these purposes in the course of screening. Cellular processes under the control of the PHD-1 signaling pathway may include, but are not limited to, normal cellular functions, proliferation, differentiation, maintenance of cell shape, and adhesion, in addition to abnormal or potentially deleterious processes such as unregulated cell proliferation, loss of contact inhibition, blocking of differentiation or cell death. The qualitative or quantitative observation and measurement of any of the described cellular processes by techniques known in the art may be advantageously used as a means of scoring for signal transduction in the course of screening.

Random peptide libraries, such as tetrameric peptide libraries, consisting of all possible combinations of amino acids attached to a solid phase support may be used to identify peptides that are able to bind to the ligand binding site of a given receptor or other functional domains of a receptor such as kinase domains (K. S. Lam et al., 1991, *Nature* 354:82).

Also within the scope of the invention are the use oligonucleotide sequences that include anti-sense RNA and DNA molecules and ribozymes that function to inhibit the translation of PHD-1 mRNA. Anti-sense RNA and DNA molecules act to directly block the translation of mRNA by binding to targeted mRNA and preventing protein translation. Ribozymes are enzymatic RNA molecules capable of catalyzing the specific cleavage of RNA. The mechanism of ribozyme action involves sequence-specific hybridization of the ribozyme molecule to complementary target RNA of PHD-1, followed by an endonucleolytic cleavage. Within the scope of the invention are engineered hammerhead motif ribozyme molecules that specifically and efficiently catalyze endonucleolytic cleavage of PHD-1 RNA sequences.

Specific ribozyme cleavage sites within any potential RNA target are initially identified by scanning the target molecule for ribozyme cleavage sites that include the following sequences: GUA, GUU and GUC. Once identified, short RNA sequences of between 15 and 20 ribonucleotides corresponding to the region of the target gene containing the cleavage site may be evaluated for predicted structural features such as a secondary structure that may render the oligonucleotide sequence unsuitable. The suitability of candidate targets may also be evaluated by testing their accessibility to hybridization with complementary oligonucleotides, using ribonuclease protection assays.

Both anti-sense RNA and DNA molecules and ribozymes of the invention may be prepared by any method known in the art for the synthesis of RNA molecules. These include techniques for chemically synthesizing oligodeoxyribonucleotides well known in the art such as, for example, solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize anti-sense RNA constitutively or inducibly, depending on the promoter used, can be introduced stably into cell lines.

Beside the inhibition of translation, the anti-sense oligonucleotide sequences can work through the use of RNA inhibition (RNAi) with the invention applying anti-sense oligonucleotides that are specifically directed to the sequence that encodes PHD-1 and forms a siRNA duplex. RNAi is based on the degradation of particular target sequences by the design of short interference RNA oligos (siRNA) that recognize the target sequence and subsequently trigger their degradation by a poorly understood pathway. The siRNA duplexes should preferentially be shorter than 30 nucleotides, because longer stretches of dsRNA can activate the PKR pathway in mammalian cells, which results in a global a-specific shut-down of protein synthesis. Target regions should be AA(N19)TT or AA(N21), should be specific for the gene of interest and should have a GC content of approximately 50%. The siRNAs duplexes can, for example, be transfected in the cells of interest by oligofectamin (Life Technologies) and the transfection efficiency reaches 90-95%.

In certain embodiments, the invention also aims at a method for the treatment of skeletal muscle degenerative diseases by administering to a patient in need of such treatment an effective amount of an LNA-modified antisense oligonucleotide (LNA stands for locked nucleic acid), or a cocktail of different LNA-modified antisense oligonucleotides, or a cocktail of different LNA-modified and unmodified antisense oligonucleotides specific for the PHD-1 gene.

An LNA-modified oligonucleotide contains one or more units of an LNA monomer, preferably one or more 2'-O, 4'-C-methylene bridge monomers (oxy-LNA), see WO9914220. Incorporation of LNA monomers containing a 2'-O, 4'-C-methylene bridge into an oligonucleotide sequence leads to an improvement in the hybridization stability of the modified oligonucleotide. Oligonucleotides comprising the 2'-O, 4'-C-methylene bridge (LNA) monomers and also the corresponding 2'-thio-LNA (thio-LNA), 2'-HN-LNA (amino-LNA), and 2'-N(R)-LNA (amino-R-LNA) analogue, form duplexes with complementary DNA and RNA with thermal stabilities not previously observed for bi- and tricyclic nucleosides modified oligonucleotides.

The increase in $T_m$ per modification varies from +3 to +11 degree Celsius, and furthermore, the selectivity is also improved. An LNA-modified oligonucleotide may contain other LNA units in addition to or in place of an oxy-LNA group. In particular, preferred additional LNA units include 2'-thio-LNA (thio-LNA), 2'-HN-LNA (amino-LNA), and 2'-N(R)-LNA (amino-R-LNA)) monomers in either the D-beta or L-alpha configurations or combinations thereof. An LNA-modified oligonucleotide may also have internucleoside linkages other than the native phosphodiester, e.g., phosphoromonothioate, phosphorodithioate, and methylphosphonate linkages. The LNA-modified oligonucleotide can be fully modified with LNA (i.e., each nucleotide is an LNA unit), but it is generally preferred that the LNA-modified oligomers will contain other residues such as native DNA monomers, phosphoromonothioate monomers, methylphosphonate monomers or analogs thereof. In general, an LNA-modified oligonucleotide will contain at least about 5, 10, 15 or 20 percent LNA units, based on total nucleotides of the oligonucleotide, more typically at least about 20, 25, 30, 40, 50, 60, 70, 80 or 90 percent LNA units, based on total bases of the oligonucleotide.

An LNA-modified oligonucleotide used in accordance with the invention suitably is at least a 5-mer, 6-mer, 7-mer, 8-mer, 9-mer or 10-mer oligonucleotide, that is, the oligonucleotide is an oligomer containing at least 5, 6, 7, 8, 9, or 10 nucleotide residues, more preferably at least about 11 or 12 nucleotides. The preferred maximum size of the oligonucleotide is about 40, 50 or 60 nucleotides, more preferably up to about 25 or 30 nucleotides, and most preferably about between 12 and 20 nucleotides. While oligonucleotides smaller than 10-mers or 12-mers may be utilized, they are more likely to hybridize with non-targeted sequences (due to the statistical possibility of finding exact sequence matches by chance in the human genome of $3.10^9$ bp), and for this reason may be less specific. In addition, a single mismatch may destabilize the hybrid, thereby impairing its therapeutic function. While oligonucleotides larger than 40-mers may be utilized, synthesis, and cellular uptake may become somewhat more troublesome, although specialized vehicles or oligonucleotide carriers will improve cellular uptake of large oligomers. Moreover, partial matching of long sequences may lead to non-specific hybridization and non-specific effects.

While, in principle, oligonucleotides having a sequence complementary to any region of the target mRNA of PHD-1 find utility as described herein, preferred are oligonucleotides capable of forming a stable duplex with a portion of the transcript lying within about 50 nucleotides (preferably within about 40 nucleotides) upstream (the 5' direction), or about 50 (preferably 40) nucleotides downstream (the 3' direction) from the translation initiation codon of the target mRNA. Also preferred are oligonucleotides that are capable of forming a stable duplex with a portion of the target mRNA transcript including the translation initiation codon.

LNA-modified oligonucleotides based on the PHD-1 sequence can be used for the treatment of skeletal muscle degenerative diseases. In general, therapeutic methods of the invention for the treatment of skeletal muscle degenerative diseases include administration of a therapeutically effective amount of an LNA-modified oligonucleotide to a mammal, particularly a human. In antisense therapies, administered LNA-modified oligonucleotide contacts (interacts) with the targeted PHD-1 RNA from the gene, whereby expression of PHD-1 is inhibited and inhibition of the degeneration of skeletal muscle cells is induced. Such inhibition of PHD-1 expression suitably will be at least a 10% or 20% difference relative to a control, more preferably at least a 30%, 40%, 50%, 60%, 70%, 80%, or 90% difference in expression relative to a control. It will be particularly preferred where interaction or contact with an LNA-modified oligonucleotide results in complete or essentially complete inhibition of expression relative to a control, e.g., at least about a 95%, 97%, 98%, 99% or 100% inhibition of expression relative to a control. A control sample for determination of such modulation can be comparable cells (in vitro or in vivo) that have not been contacted with the LNA-modified oligonucleotide. The monitoring of the % inhibition of PHD-1 expression can be followed by the % survival of skeletal muscle cells since the two inhibition processes are inversely correlated.

In certain embodiments, the above-described molecules that are capable of neutralizing the activity of PHD-1 can be used for manufacturing a medicament to treat skeletal muscle degenerative diseases.

In certain embodiments, the above-described molecules that are capable of neutralizing the activity of PHD-1 can be used for manufacturing a medicament to prevent and/or to treat skeletal fiber injury.

The term "skeletal muscle degenerative diseases" comprises any of a group of diseases where degeneration (atrophy) occurs of skeletal muscle cells. A serious indication where skeletal muscle degeneration takes place is due to ischemic insults. For example, it has become increasingly recognized that skeletal muscle atrophy is common in patients with chronic pulmonary disease (COPD). Another example where skeletal muscle atrophy occurs is critical limb ischemia (CLI), which is a disease manifested by sharply diminished blood flow to the legs. Up to 10 million people in the United States alone suffer from severe leg pain (claudication) and non-healing-ulcers (peripheral vascular disease), both of which can ultimately lead to CLI. The most common causes that can lead to CLI are atherosclerosis and embolization (e.g., a clot that has been ejected from a failing heart, or from an aneurysm in the aorta, into the leg). The invention also shows that inhibitors of PHD-1 can be used for skeletal muscle preservation during transient ischemic conditions that can occur, for example, during an operation.

Yet another class of skeletal muscle degenerative diseases is muscle pathologies associated with a reduced glycolytic rate such as McArdle's disease and phosphofructokinase disease (PFKD). Yet another class comprises muscle atrophy, which occurs due to muscle denervation. In such denervation atrophy, a lack of tonic stimuli occurs and muscle cells become atrophic. Causes of denervation atrophy include localized loss of nerve function (neuritis) or generalized loss of the entire motor unit. After denervation, muscles become rapidly atrophic and 50% of muscle mass could be lost in just a few weeks. Another class of such diseases comprises muscle degeneration, which occurs due to immobilization. "Immobilization" means here that the skeletal muscle system is unloaded because of, for example, prolonged space flight, during conservative treatment after sports injuries or by a plaster cast after orthopedic surgery. This immobilization causes a serious atrophy of muscle mass leading to a decrease in physical performance and high-power output capacity. Yet another class of such diseases where muscle degeneration takes place comprises muscular dystrophies. These disorders include a progressive wasting of skeletal muscle. The most common examples are Duchenne and Becker muscular dystrophy. Yet another class of conditions where muscle degeneration takes place comprises critical illness. Critical illness (e.g., burns, sepsis) is associated with a serious muscle wasting and muscle weakness.

The invention not only aims at using the PHD-1 inhibitory molecules for treatment of humans but also aims at using these molecules for veterinary diseases and conditions. Common causes of myopathies (degenerative diseases of muscle) in animals that can also be treated with PHD-1 inhibitors are: (1) metabolic myopathies (e.g., porcine stress syndrome, malignant hyperthermia and pale soft exudative pork), (2) exertional myopathies, which comprise a group of diseases that result in severe muscle degeneration following strenuous exercise (e.g., azoturia and tying-up in horses, greyhound myopathy in dogs, capture myopathy in wild animals and compartment syndrome in poultry), (3) traumatic myopathies (e.g., Downer syndrome, which is an ischemic necrosis of ventral and limb muscles following prolonged recumbency (disease/anesthesia), and Crush syndrome).

The term "medicament to treat" relates to a composition comprising molecules as described above and a pharmaceutically acceptable carrier or excipient (both terms can be used interchangeably) to treat skeletal muscle degenerative diseases. Suitable carriers or excipients known to the skilled man are saline, Ringer's solution, dextrose solution, Hank's solution, fixed oils, ethyl oleate, 5% dextrose in saline, substances that enhance isotonicity and chemical stability, buffers and preservatives. Other suitable carriers include any carrier that does not itself induce the production of antibodies harmful to the individual receiving the composition such as proteins, polysaccharides, polylactic acids, polyglycolic acids, polymeric amino acids and amino acid copolymers. The "medicament" may be administered by any suitable method within the knowledge of the skilled man. The preferred route of administration is parenterally.

In parental administration, the medicament of this invention will be formulated in a unit dosage injectable form such as a solution, suspension or emulsion, in association with the pharmaceutically acceptable excipients as defined above. However, the dosage and mode of administration will depend on the individual. Generally, the medicament is administered so that the protein, polypeptide, peptide or siRNA of the invention is given at a dose between 1 µg/kg and 10 mg/kg, more preferably between 10 µg/kg and 5 mg/kg, most preferably between 0.1 and 2 mg/kg. Preferably, it is given as a bolus dose. Continuous infusion may also be used and includes continuous subcutaneous delivery via an osmotic minipump. If so, the medicament may be infused at a dose between 5 and 20 µg/kg/minute, more preferably between 7 and 15 µg/kg/minute.

It is clear to the person skilled in the art that the use of a therapeutic composition comprising, for example, an antibody against PHD-1 or an LNA capable of binding to PHD-1 for the manufacture of a medicament to treat skeletal muscle degenerative diseases can be administered by any suitable means, including but not limited to, parenteral, subcutaneous, intraperitoneal, intrapulmonary, and intranasal administration. Parenteral infusions include intramuscular, intravenous, intra-arterial, intraperitoneal, or subcutaneous administration. In addition, the therapeutic composition is suitably administered by pulse infusion, particularly with declining doses of the antibody. Preferably, the therapeutic composition is given by injections, most preferably intravenous or subcutaneous injections, depending in part on whether the administration is brief or chronic.

Another aspect of administration for treatment is the use of gene therapy to deliver the above-mentioned anti-sense gene or functional parts of the PHD-1 gene or a ribozyme directed against the PHD-1 mRNA or a functional part thereof or a construct encoding an siRNA against PHD-1. Gene therapy means the treatment by the delivery of therapeutic nucleic acids to a patient's skeletal muscle cells. This is extensively reviewed in Lever and Goodfellow 1995; *Br. Med Bull.,* 51:1-242; Culver 1995; F. D. Ledley, 1995, *Hum. Gene Ther.* 6:1129. There are two general approaches to achieve gene delivery; these are non-viral delivery and virus-mediated gene delivery.

In certain embodiments, provided is a non-human transgenic animal whose genome comprises a disruption in the endogenous PHD-1 gene wherein the disruption results in a decreased expression or a lack of expression of the endogenous PHD-1 gene.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with a recombinant vector. The term "transgenic animal" is not meant to encompass classical cross-breeding or in vitro fertilization, but rather is meant to encompass animals in which one or more cells are altered by or receive a recombinant DNA molecule as described above. The latter molecule may be specifically targeted to a defined genetic locus, be randomly integrated within a chromosome, or it may be extra-chromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring in fact, possess some or all of that alteration or genetic information, then they, too, are transgenic animals. The alteration or genetic information may be foreign to the species of animal to which the recipient belongs, or foreign only to the particular individual recipient, or may be genetic information already possessed by the recipient. In the last case, the altered or introduced gene may be expressed differently than the native gene (e.g., lack of expression in a specific organ or tissue).

In certain embodiments, provided is a transgenic, non-human animal characterized by having an endogenous nucleic acid sequence encoding a non-functional PHD-1, wherein non-functional PHD-1 expression is in a specific tissue or in a specific organ.

Thus, in other words, provided is a transgenic non-human animal in which in at least one organ or tissue, the PHD-1 gene has been selectively inactivated. In a preferred embodiment, the non-functional expression of the PHD-1 gene is in the skeletal muscle. Mice comprising conditionally targeted PHD-1 (PHD-$1^{flx/flx}$) can be crossed with mice expressing Cre recombinase under the transcriptional control of promoters that drive selective Cre expression in skeletal muscle cells. More specifically, provided is a transgenic non-human animal whose genome comprises a disruption in the PHD-1 gene, wherein the transgenic animal exhibits a decreased level or no functional PHD-1 protein relative to wild-type. The non-human animal may be any suitable animal (e.g., cat, cattle, dog, horse, goat, rodent, and sheep), but is preferably a rodent. More preferably, the non-human animal is a rat or a mouse.

Unless otherwise indicated, the term "PHD-1 gene" refers herein to a nucleic acid sequence encoding PHD-1 protein and any allelic variants thereof. Due to the degeneracy of the genetic code, the PHD-1 gene of the invention includes a multitude of nucleic acid substitutions that will also encode a PHD-1 protein. An "endogenous" PHD-1 gene is one that originates or arises naturally, from within an organism. Additionally, as used herein, "PHD-1 protein" includes both a "PHD-1 protein" and a "PHD-1 protein analogue." A "PHD-1 analogue" is a functional variant of the "PHD-1 protein," having PHD-1-protein biological activity that has 60% or greater (preferably, 70% or greater) amino-acid-sequence homology with the PHD-1 protein, as well as a fragment of the PHD-1 protein having PHD-1-protein biological activity.

In certain embodiments, provided are cell lines derived from the above-described transgenic animals, in particular, cell lines lacking PHD-1. In certain embodiments, the cells are skeletal muscle cells. As further used herein, the term "transgene" refers to a nucleic acid (e.g., DNA or a gene) that has been introduced into the genome of an animal by experimental manipulation, wherein the introduced gene is not endogenous to the animal, or is a modified or mutated form of a gene that is endogenous to the animal. The modified or mutated form of an endogenous gene may be produced through human intervention (e.g., by introduction of a point mutation, introduction of a frameshift mutation, deletion of a portion or fragment of the endogenous gene, insertion of a selectable marker gene, insertion of a termination codon, insertion of recombination sites, etc.). A transgenic non-human animal may be produced by several methods involving human intervention, including, without limitation, introduction of a transgene into an embryonic stem cell, newly fertilized egg, or early embryo of a non-human animal; integration of a transgene into a chromosome of the somatic and/or germ cells of a non-human animal; and any of the methods described herein.

Such a transgenic animal has a genome in which the PHD-1 gene has been selectively inactivated, resulting in a disruption in its endogenous PHD-1 gene in at least one tissue or organ. As used herein, a "disruption" refers to a mutation (i.e., a permanent, transmissible change in genetic material) in the PHD-1 gene that prevents normal expression of functional PHD-1 protein (e.g., it results in expression of a mutant PHD-1 protein, it prevents expression of a normal amount of PHD-1 protein, or it prevents expression of PHD-1 protein). Examples of a disruption include, without limitation, a point mutation, introduction of a frameshift mutation, deletion of a portion or fragment of the endogenous gene, insertion of a selectable marker gene, and insertion of a termination codon. As used herein, the term "mutant" refers to a gene (or its gene product) that exhibits at least one modification in its sequence (or its functional properties) as compared with the wild-type gene (or its gene product). In contrast, the term "wild-type" refers to the characteristic genotype (or phenotype) for a particular gene (or its gene product) as found most frequently in its natural source (e.g., in a natural population). A wild-type animal, for example, expresses functional PHD-1.

Selective inactivation of a gene in a transgenic non-human animal may be achieved by a variety of methods and may result in either a heterozygous disruption (wherein one PHD-1 gene allele is disrupted, such that the resulting transgenic animal is heterozygous for the mutation) or a homozygous disruption (wherein both PHD-1 gene alleles are disrupted, such that the resulting transgenic animal is homozygous for the mutation). In one embodiment of the invention, the endogenous PHD-1 gene of the transgenic animal is disrupted through homologous recombination with a nucleic acid sequence that encodes a region common to PHD-1 gene products. By way of example, the disruption through homologous recombination may generate a knock-out mutation in the PHD-1 gene, particularly a knock-out mutation wherein at least one deletion has been introduced into at least one exon of the PHD-1 gene. In a preferred embodiment of the invention, the knock-out mutation is generated in a coding exon of the PHD-1 gene.

Additionally a disruption in the PHD-1 gene may result from insertion of a heterologous selectable marker gene into the endogenous PHD-1 gene. As used herein, the term "selectable marker gene" refers to a gene encoding an enzyme that confers upon the cell or organism in which it is expressed a resistance to a drug or antibiotic, such that expression or activity of the marker can be selected for (e.g., a positive marker, such as the neo gene) or against (e.g., a negative marker, such as the dt gene). As further used herein, the term "heterologous selectable marker gene" refers to a selectable marker gene that, through experimental manipulation, has been inserted into the genome of an animal in which it would not normally be found.

The transgenic non-human animal exhibits decreased expression of functional PHD-1 protein relative to a corresponding wild-type non-human animal of the same species. As used herein, the phrase "exhibits decreased expression of functional PHD-1 protein" refers to a transgenic animal in which the detected amount of functional PHD-1 is less than that which is detected in a corresponding animal of the same species whose genome contains a wild-type PHD-1 gene. Preferably, the transgenic animal contains at least 90% less functional PHD-1 than the corresponding wild-type animal. More preferably, the transgenic animal contains no detectable, functional PHD-1 as compared with the corresponding wild-type animal. Levels of PHD-1 in an animal, as well as PHD-1 activity, may be, for example, detected using appropriate antibodies against the PHD-1 protein.

Accordingly, where the transgenic animal of the invention exhibits decreased expression of functional PHD-1 protein relative to wild-type, the level of functional PHD-1 protein in the transgenic animal is lower than that which otherwise would be found in nature. In one embodiment of the invention, the transgenic animal expresses mutant PHD-1 (regardless of amount). In certain embodiments of the invention, the transgenic animal expresses no PHD-1 (wild-type or mutant). In certain embodiments of the invention, the transgenic animal expresses wild-type PHD-1 protein, but at a decreased level of expression relative to a corresponding wild-type animal of the same species.

The transgenic, non-human animal of the invention, or any transgenic, non-human animal exhibiting decreased expression of functional PHD-1 protein relative to wild-type, may be produced by a variety of techniques for genetically engineering transgenic animals. For example, to create a transgenic, non-human animal exhibiting decreased expression of functional PHD-1 protein relative to a corresponding wild-type animal of the same species, a PHD-1 targeting vector is generated first.

As used herein, the term "PHD-1 targeting vector" refers to an oligonucleotide sequence that comprises a portion, or all, of the PHD-1 gene, and is sufficient to permit homologous recombination of the targeting vector into at least one allele of the endogenous PHD-1 gene within the recipient cell. In one embodiment of the invention, the targeting vector further comprises a positive or negative heterologous selectable marker gene (e.g., the positive selection gene, neo). Preferably, the targeting vector may be a replacement vector (i.e., the selectable marker gene replaces an endogenous target gene). Such a disruption is referred to herein as a "null" or "knock-out" mutation. By way of example, the PHD-1 targeting vector may be an oligonucleotide sequence comprising at least a portion of a non-human PHD-1 gene in which there is at least one deletion in at least one exon. In certain embodiments, the PHD-1 targeting vector comprises recombination sites (e.g., loxP sites or FRT sites) that do not interrupt the coding region of the PHD-1 gene.

In the method of the invention, the PHD-1 targeting vector that has been generated may then be introduced into a recipient cell (comprising a wild-type PHD-1 gene) of a non-human animal to produce a treated recipient cell. This introduction may be performed under conditions suitable for homologous recombination of the vector into at least one of the wild-type PHD-1 genes in the genome of the recipient cell. The non-human animal may be any suitable animal (e.g., cat, cattle, dog, horse, goat, rodent, and sheep), as described above, but is preferably a rodent. More preferably, the non-human animal is a rat or a mouse. The recipient cell may be, for example, an embryonic stem cell, or a cell of an oocyte or zygote.

The PHD-1 targeting vector of the invention may be introduced into the recipient cell by any in vivo or ex vivo means suitable for gene transfer, including, without limitation, electroporation, DEAE Dextran transfection, calcium phosphate transfection, lipofection, monocationic liposome fusion, polycationic liposome fusion, protoplast fusion, creation of an in vivo electrical field, DNA-coated microprojectile bombardment, injection with recombinant replication-defective viruses, homologous recombination, viral vectors, and naked DNA transfer, or any combination thereof. Recombinant viral vectors suitable for gene transfer include, but are not limited to, vectors derived from the genomes of viruses such as retrovirus, HSV, adenovirus, adeno-associated virus, Semliki Forest virus, cytomegalovirus, and vaccinia virus.

In accordance with the methods of the invention, the treated recipient cell then may be introduced into a blastocyst of a non-human animal of the same species (e.g., by injection or microinjection into the blastocell cavity), to produce a treated blastocyst. Thereafter, the treated blastocyst may be introduced (e.g., by transplantation) into a pseudopregnant non-human animal of the same species, for expression and subsequent germline transmission to progeny. For example, the treated blastocyst may be allowed to develop to term, thereby permitting the pseudopregnant animal to deliver progeny comprising the homologously recombined vector, wherein the progeny may exhibit decreased expression of PHD-1 relative to corresponding wild-type animals of the same species. It then may be possible to identify a transgenic non-human animal whose genome comprises a disruption in its endogenous PHD-1 gene. The identified transgenic animal may then be interbred with other founder transgenic animals to produce heterozygous or homozygous non-human animals exhibiting decreased expression of functional PHD-1 protein relative to corresponding wild-type animals of the same species.

A type of recipient cell for transgene introduction is the embryonal stem cell (ES). ES cells may be obtained from pre-implantation embryos cultured in vitro. Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

As used herein, a "targeted gene" or "knock-out" is a DNA sequence introduced into the germline of a non-human animal by way of human intervention, including, but not limited to, the methods described herein. The targeted genes of the invention include DNA sequences that are designed to specifically alter cognate endogenous alleles.

In order to produce the gene constructs used as described herein, recombinant DNA and cloning methods, which are well known to those skilled in the art, may be utilized (see Sambrook et al., 1989, *Molecular Cloning, A Laboratory Manual*, 2nd Ed., Cold Spring Harbor Laboratory Press, NY). In this regard, appropriate PHD-1 coding sequences may be generated from genomic clones using restriction enzyme sites that are conveniently located at the relevant positions within the PHD-1 sequence. Alternatively, or in conjunction with the method above, site-directed mutagenesis techniques involving, for example, either the use of vectors such as M13 or phagemids, which are capable of producing single-stranded circular DNA molecules, in conjunction with synthetic oligonucleotides and specific strains of *Escherichia coli* (*E. coli*) (T. A. Kunkel et al., 1987, *Meth. Enzymol.* 154:367-382) or the use of synthetic oligonucleotides and PCR (polymerase chain reaction) (Ho et al., 1989, *Gene* 77:51-59; M. Kamman et al., 1989, *Nucl. Acids Res.* 17:5404) may be utilized to generate the necessary PHD-1 nucleotide coding sequences. Appropriate PHD-1-sequences may then be isolated, cloned, and used directly to produce transgenic animals. The sequences may also be used to engineer the chimeric gene constructs that utilize regulatory sequences other than the PHD-1 promoter, again using the techniques described here. These chimeric gene constructs can then also be used in the production of transgenic animals.

In certain embodiments, a non-human, transgenic animal comprising a targeting vector that further comprises recombination sites (e.g., Lox sites, FRT sites) can be crossed with a non-human, transgenic animal comprising a recombinase (e.g., Cre recombinase, FLP recombinase) under control of a particular promoter. It has been shown that these site-specific recombination systems, although of microbial origin for the majority, function in higher eukaryotes, such as plants, insects and mice. Among the site-specific recombination systems commonly used, there may be mentioned the Cre/Lox and FLP/FRT systems. The strategy normally used consists of inserting the loxP (or FRT) sites into the chromosomes of ES cells by homologous recombination, or by conventional transgenesis, and then of delivering Cre (or FLP) for the latter to catalyze the recombination reaction. The recombination between the two loxP (or FRT) sites may be obtained in ES cells or in fertilized eggs by transient expression of Cre or using a Cre transgenic mouse. Such a strategy of somatic mutagenesis allows a spatial control of the recombination because the expression of the recombinase is controlled by a promoter specific for a given tissue or for a given cell.

A second strategy consists in controlling the expression of recombinases over time so as to allow temporal control of somatic recombination. To do this, the expression of the recombinases is controlled by inducible promoters such as the interferon-inducible promoter, for example. The coupling of the tetracycline-inducible expression system with the site-specific recombinase system described in WO 94/04672 has made it possible to develop a system for somatic modification of the genome, which is controlled spatiotemporally. Such a system is based on the activation or repression, by tetracycline, of the promoter controlling the expression of the recombinase gene. It has been possible to envisage a new strategy following the development of chimeric recombinases selectively activated by the natural ligand for the estrogen receptor. Indeed, the observation that the activity of numerous proteins, including at least two enzymes (the tyrosine kinases c-abl and src), is controlled by estrogens, when the latter is linked to the ligand-binding domain (LBD) of the estrogen receptor alpha, has made it possible to develop strategies for spatiotemporally controlled site-specific recombination. The feasibility of the site-specific somatic recombination activated by an anti-estrogenic ligand has thus been demonstrated for "reporter" DNA sequences in mice and, in particular, in various transgenic mouse lines that express the fusion protein Cre-ER$^T$ activated by Tamoxifen. The feasibility of the site-specific recombination activated by a ligand for a gene present in its natural chromatin environment has been demonstrated in mice.

Initial screening of the transgenic animals may be accomplished by Southern blot analysis or PCR techniques to analyze animal tissues to verify that integration of the transgene has taken place. The level of mRNA expression of the transgene in the tissues of the transgenic animals may also be assessed using techniques that include, but are not limited to, Northern blot analysis of tissue samples obtained from the animal, in situ hybridization analysis, and reverse transcriptase-PCR (rt-PCR). Samples of skeletal muscle cells may be evaluated immunocytochemically using antibodies specific for PHD-1.

DETAILED DESCRIPTION OF THE INVENTION

The following examples more fully describe the invention, but are not intended to limit the invention. All of the starting materials and reagents disclosed below are known to those skilled in the art and are available commercially or can be prepared using well-known techniques.

EXAMPLES

1. Generation of PHD1$^{-/-}$, PHD2$^{-/-}$ and PHD3$^{-/-}$ Mice

Figure 1:
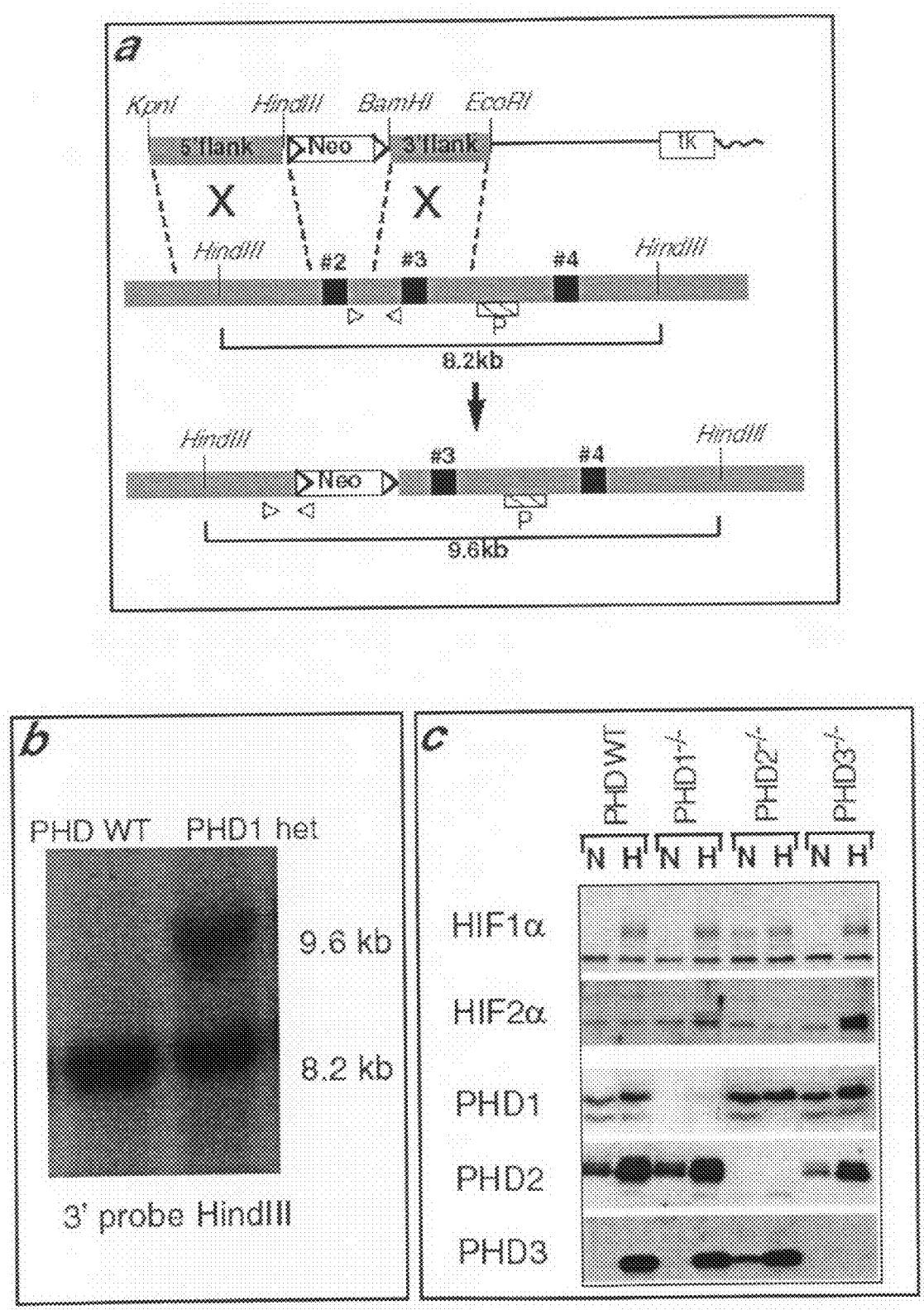
FIG. 1: Targeting of the PHD1, PHD2 and PHD3 genes. Targeting strategy of PHD1 locus inactivation. α, Top: Outline of targeting vector pKOScrambler1908 and restriction sites required for cloning of PHD1 genomic sequences as 5' and 3' flanks at both sides of neo cassette. Middle: Wild-type PHD1 allele diagram indicating relative position of exons #2, #3 and #4. Bottom: Replacement of exon 2 by neo cassette after homologous recombination. b, Southern blot analysis from recombinant ES cells. Genomic DNA was digested with HindIII and then subjected to Southern blot and hybridized with 3' external probe (P). 8.2 kb and 9.6 kb genomic fragments correspond to PHD1WT and PHD1$^{-/-}$ alleles, respectively. Location of HindIII sites and probe are indicated in (a). c, Lack of PHD1, PHD2 and PHD3 expression as a result of the targeting procedure was confirmed by Western blot analysis. Expression of all PHDs was clearly detectable in transformed WT MEFs and was absent in respective PHD$^{-/-}$ cells under both normoxic (N) and hypoxic (H) conditions. Normoxic and hypoxia-inducible expression of PHD2 and PHD3 was unaltered in PHD1$^{-/-}$ MEFs. Hypoxic (H) HIF-2α-, but not HIF-1α, expression was enhanced in PHD1$^{-/-}$ MEFs.

To inactivate the PHD1 and PHD2 genes, we constructed a targeting vector in which the second exon of each gene, which encodes part of the catalytic domain conferring the prolyl hydroxylase activity,[15] was replaced by a neomycin phosphotransferase selection cassette (FIG. 1, Panel a). To inactivate the PHD3 gene, a targeting vector was designed to delete exon 1, as well as the transcription initiation site and the proximal 5' promoter region. Each of these targeting vectors was electroporated in embryonic stem (ES) cells and correct recombination of these targeting vectors was confirmed by Southern blot analysis (FIG. 1, Panel b). Targeted ES cell clones were used to generate chimeric mice, which sired viable and healthy offspring, lacking a single allele of PHD1 (PHD1$^{+/-}$), PHD2 (PHD2$^{+/-}$) or PHD3 (PHD3$^{+/-}$). These heterozygously deficient mice were used to establish a colony of PHD1$^{-/-}$, PHD2$^{-/-}$ and PHD3$^{-/-}$ mice. By Northern and Western blot analysis of mouse embryonic fibroblasts (MEFs), PHD1, PHD2 and PHD3 transcript and protein levels were detectable in wild-type (WT) cells, while no transcripts or protein of the inactivated PHD gene could be detected in the respective homozygous PHD-deficient cells (FIG. 1, Panel c).

In order to evaluate whether the PHDs might have distinct or complementary roles, we determined the expression of each of these PHDs in MEFs of the various knock-out lines. As expected, the expression of PHD1, PHD2 and PHD3 was up-regulated by hypoxia in WT cells. Loss of PHD2 compensatorily up-regulated the expression of PHD1 and PHD3 in normoxic conditions (FIG. 1, Panel c). By contrast, deficiency of PHD1 or PHD3 did not affect the expression of the residual PHD genes (FIG. 1, Panel c). Of note, HIF-1α protein levels were increased in normoxic PHD2$^{-/-}$ cells, while HIF-2α protein levels were enhanced in hypoxic PHD1$^{-/-}$ and PHD3$^{-/-}$ cells (FIG. 1, Panel c), suggesting a specific regulation of HIF-2α expression by PHD1 and PHD3. We first determined whether loss of a PHD affected the inheritance (Table 1). PHD1$^{-/-}$ mice were born at the expected Mendelian frequencies and were healthy and fertile. PHD3$^{-/-}$ mice were slightly underrepresented at birth (the precise cause of this remains to be analyzed), but the surviving mice appeared healthy and were fertile. In contrast, loss of PHD2 resulted in embryonic lethality at mid-gestation, indicating that the critical role of PHD2 during embryonic development cannot be compensated by PHD1 and PHD3. Further phenotyping revealed that PHD2$^{-/-}$ embryos succumbed because of severe placentation defects. PHD2$^{+/-}$ mice were healthy, fertile and gained normal weight. In this study, we analyzed the distinct role of each PHD in ischemic disease in adult PHD1$^{-/-}$, PHD2$^{+/-}$ and PHD3$^{-/-}$ mice.

2. Ischemic Skeletal Muscle Injury is Attenuated in PHD1$^{-/-}$ Mice

To determine the role of the PHDs in the cellular response to hypoxia, we focused on the skeletal muscle, as ligation of the femoral artery provides a simple and reproducible model of hind limb ischemia, which has been extensively characterized previously. For a PHD to have a functional role in skeletal muscle, it should be expressed in this tissue. Immunoblotting revealed that PHD1 and PHD3 were expressed in skeletal muscle from WT mice.

Immunohistochemistry studies confirmed that nuclei of skeletal myocytes expressed PHD1 and PHD3. In contrast, PHD2 expression was undetectable in skeletal muscle; this was not due to technical limitations as PHD2 was readily detectable by Western blot analysis in cardiac muscle. In baseline conditions, muscle development appeared normal in WT, PHD1$^{-/-}$, and in PHD2$^{+/-}$ and PHD3$^{-/-}$ mice, no genotypic differences in myofiber size or muscle mass were detected. In order to determine the specific role of PHD1, PHD2 and PHD3 in ischemic muscle disease, we ligated the femoral artery. Transverse sections through the gastrocnemius muscle revealed extensive ischemic tissue damage in WT mice at seven days after femoral artery ligation. Crural muscles from PHD2$^{+/-}$ and PHD3$^{-/-}$ hind limbs also developed a comparable degree of ischemic muscle necrosis (Table 2).

In sharp contrast, ischemic PHD1$^{-/-}$ muscles predominantly contained viable skeletal muscle fibers and were largely devoid of necrotic areas (Table 2). Fibrotic scar tissue was also dramatically reduced in PHD1$^{-/-}$ hind limbs (% fibrotic area/total transverse section area: 3.7±1.9% in PHD1$^{-/-}$ versus 74.4±12.9% in WT; n=8; P<0.01). We initially thought that the healthy appearance of the PHD1$^{-/-}$ muscles after ischemia was attributable to enhanced tissue regeneration. However, staining for CD56, a marker of activated myogenic precursor cells, revealed that most satellite cells were quiescent in post-ischemic limbs of PHD1$^{-/-}$ animals, whereas multiple activated CD56-positive myogenic precursor cells were observed in the regenerating crural muscles of WT mice. Moreover, myocellular BrdU uptake was not enhanced in PHD1$^{-/-}$ muscles following ischemia, and muscle fibers did not have a central nucleus, a characteristic histo-pathological feature of muscle regeneration. We therefore suspected that the observed effect was caused by tissue protection, rather than by enhanced muscle regeneration.

Indeed, analysis of semi-thin sections at four hours after induction of ischemia revealed progressive myofiber edema and sarcomere loss in WT limbs, whereas striated muscle fibers appeared intact and healthy in PHD1$^{-/-}$ mice. Consistently, extensive coagulation necrosis dominated the histological picture in WT but not in PHD1$^{-/-}$ mice at 48 hours after induction of ischemia. Moreover, in WT mice, labeling of the intermediate filament desmin was absent or weak, indicative of filament protein breakdown due to impaired skeletal muscle viability. In contrast, desmin was detected throughout all fibers of the ischemic PHD1$^{-/-}$ gastrocnemius muscle at 48 hours after induction of ischemia. Morphometric quantification after 48 hours of ischemia revealed more desmin-immunopositive areas and more intense staining in PHD1$^{-/-}$ than in WT gastrocnemius muscle (% relative desmin-positive area/optical field: 7.1±1.2% in PHD1$^{-/-}$ versus 1.7±0.7% in WT; n=4; P<0.01). Thus, loss of PHD1, but not of PHD2 or PHD3, significantly protected the mice against ischemic muscle necrosis.

3. Vascular Perfusion of the Hind Limb is not Altered in PHD1$^{-/-}$ Mice

To elucidate the mechanisms of muscle protection in PHD1$^{-/-}$ mice, we first sought to determine whether deficiency of PHD1 increased vascular perfusion of the hind limbs in baseline conditions or after ischemia (a likely mechanism when considering that loss of PHD1 increased the levels of the pro-angiogenic HIF-2α). In baseline conditions, the mean capillary density in the gastrocnemius muscle was comparable in WT and PHD1$^{-/-}$ mice (capillary/muscle fiber ratio: 1.93±0.1 in PHD1$^{-/-}$ versus 1.97±0.1 in WT mice; n=7).

Vascular microcomputed tomography (CT) imaging further revealed a normal anatomical pattern of the crural arterial branches in hind limbs of PHD1$^{-/-}$ mice, without evidence for supernumerary collateral vessels. Accordingly, functional vascular perfusion of the gastrocnemius muscle, as assessed by administration of fluorescent microspheres, was similar in PHD1$^{-/-}$ and WT mice (microspheres in the gastrocnemius muscle ml×g−1×min−1 at baseline conditions: 0.35±0.03 in PHD1$^{-/-}$ versus 0.39±0.02 in WT mice; P=0.3; n=6).

Revascularization of the ischemic hind limb involves growth of collateral arteries in the adductor muscle in the upper hind limb and capillary vessel growth in the gastrocnemius muscle in the lower hind limb. Morphometric analysis of collateral arterial growth at seven days after hind limb ischemia revealed that the total number of collateral side branches was not increased in the adductor region of PHD1$^{-/-}$ limbs (second-generation collateral side branches/mm$^2$: 22.5±5 in PHD1$^{-/-}$ versus 22.7±3.1 in WT limbs; n=7). The collateral perfusion area, representing the sum of the luminal areas of all secondary and tertiary collaterals, was also not significantly altered in PHD1$^{-/-}$ limbs (total collateral perfusion area in μm$^2$/mm$^2$: 2,560±241 in PHD1$^{-/-}$ versus 2,290±282 in WT limbs; n=7; P=n.s.). The mean capillary density in the gastrocnemius muscle was comparable in WT and PHD1$^{-/-}$ mice in viable muscle areas after seven days of ischemia (capillaries/mm$^2$: 702±56 in PHD1$^{-/-}$ versus 721±80 in WT mice; n=7).

Vascular microcomputed tomography (CT) imaging further revealed a comparable degree of residual perfusion of the popliteal artery via collateral vessels after femoral artery ligation in both genotypes. Residual blood supply to the lower hind limb was additionally determined by administration of fluorescent microspheres at various time points following vascular ligation, and was comparable in PHD1$^{-/-}$ and WT mice (microspheres in the gastrocnemius muscle ml×g−1× min−1 after 2 hours ischemia: 0.15±0.03 in PHD1$^{-/-}$ versus 0.13±0.04 in WT mice; P=0.74; n=4). Thus, loss of PHD1 did not result in an increased vascular supply. Collectively, these data suggest that skeletal muscle protection in PHD1$^{-/-}$ mice was not attributable to an increased baseline perfusion or an enhanced compensatory angiogenic response after ischemia. Instead, inactivation of the PHD1 gene preserved skeletal muscle against ischemic insult via an angiogenesis-independent mechanism.

4. Ischemic PHD1$^{-/-}$ Limbs Maintain Sufficient Levels of Energy-Rich Phosphates The lack of any vascular or regenerative defects in PHD1$^{-/-}$ limbs prompted us to consider that loss of PHD1 might perhaps change the metabolism and thereby protect against muscle ischemia. High energy phosphates, in particular ATP, are critical to secure cell functioning and viability. In ischemic conditions, skeletal muscle ATP levels are initially maintained through a rapid hydrolyzation of phosphocreatine (PCr) by creatine kinase, an enzyme transferring high-energy phosphates from PCr to ADP to generate ATP. To estimate the availability and turnover of energy-rich phosphates in the hind limb musculature of PHD1$^{-/-}$ and WT mice, we recorded in vivo $^{31}$phosphorus magnetic resonance spectra. In WT mice, PCr levels progressively declined within 30-120 minutes after onset of ischemia, while inorganic phosphate (Pi) levels steadily increased, reflecting continuous ATP utilization and insufficient ATP regeneration. In PHD1$^{-/-}$ limbs, by contrast, muscular PCr contents also decreased but only to 50% of its baseline levels and only during the initial 30 minutes after onset of ischemia, but subsequently stabilized and even seemed to recover during prolonged ischemia. Accordingly, PCr- and ATP-levels were substantially higher in PHD1$^{-/-}$ than in WT limbs at 24 hours after the ischemic insult. Thus, loss of PHD1 prevents complete energy exhaustion in ischemic limbs and thereby protects skeletal muscle against ischemic damage.

5. Normal Anaerobic Glycolysis in Ischemic PHD1$^{-/-}$ Skeletal Muscle

We therefore studied the mechanisms whereby PHD1$^{-/-}$ myofibers were capable of restoring their energy sources in conditions of low oxygen. We first hypothesized that anaerobic glycolysis was enhanced in PHD1$^{-/-}$ skeletal muscle and, therefore, studied, by micro-PET imaging, the uptake of blood-borne glucose into the gastrocnemius muscle. Muscular glucose uptake was markedly increased at one to two hours after vascular ligation in both WT and PHD1$^{-/-}$ mice, reflecting a reactive response to compensate for insufficient energy supply after femoral artery ligation. However, this compensatory response was comparable in both genotypes (glucose uptake as % injected radioactivity/g: 0.39±0.07 in PHD1$^{-/-}$ versus 0.39±0.04 in WT in baseline conditions; 0.9±0.3 in PHD1$^{-/-}$ versus 1.1±0.3 in WT at one to two hours post-ligation; n=4; P=NS). Compared to baseline conditions, glucose uptake was increased by 2.4±0.4 fold in PHD1$^{-/-}$ mice versus 2.78±0.84 fold in WT mice (n=5; p=NS). Accordingly, baseline mRNA levels of the skeletal muscle glucose transporters Glut1 and Glut4 also did not differ significantly in PHD1$^{-/-}$ and WT mice (mRNA copies per 1,000 mRNA copies of β-actin: for Glut1, 14±3 in PHD1$^{-/-}$ versus 24±5 in WT; for Glut4, 13±1.5 in PHD1$^{-/-}$ versus 12.8±2.5 in WT; n=6; P=NS).

By immunostaining, translocation of insulin-dependent Glut4-positive vesicles to the sarcolemma was comparably increased in myofibers of both genotypes at six hours after induction of ischemia. Moreover, blood glucose levels were similar in PHD1$^{-/-}$ mice shortly after ischemia (mg/dL: 413.8±75.3 in PHD1$^{-/-}$ versus 373.8±80.1 in WT; n=5; P=NS). Thus, genotypic changes in glucose uptake could not explain the preservation of high energy phosphate stores in PHD1$^{-/-}$ mice. In order to address whether glycolysis itself was enhanced in ischemic PHD1$^{-/-}$ muscle, in a first experiment, we assessed levels of the final anaerobic glycolysis metabolite lactate by proton spectroscopy. Lactate levels were considerably induced after one to two hours of ischemia in both PHD1$^{-/-}$ and WT mice (lactate content in baseline gastrocnemius: 11.7±1.1 in PHD1$^{-/-}$ versus 12.7±0.7 in WT; n=5; P=NS; gastrocnemius lactate content one to two hours post-ligation: 79.4±2.8 in PHD1$^{-/-}$ versus 80.2±14.06 in WT; n=3; P=NS). Altogether, these data reveal a rapid compensatory induction of anaerobic glycolysis to enhance muscular ATP generation in acute ischemia, but this response was not significantly more effective in PHD1$^{-/-}$ mice.

6. Mitochondrial Performance is Preserved in Ischemic PHD1−/− Skeletal Muscle As mitochondria are critical for proper electron transfer and production of ATP, and ischemia may cause mitochondrial damage, we also analyzed whether loss of PHD1 might affect (i.e., preserve better) mitochondrial function using various complementary methods. We first analyzed whether the elevated lactate levels returned to baseline levels at later stages after ischemia, as persistent lactate accumulation might indirectly reflect mitochondrial dysfunction.

Notably, when analyzed at six hours post-ischemia, elevated lactate levels persisted in ischemic WT muscle, but returned to baseline levels in PHD1$^{-/-}$ mice (lactate content in ischemic gastrocnemius at six hours post-ligation: 12.4±0.4 in PHD1$^{-/-}$ versus 95.7±43.1 in WT; n=3). We also determined succinate levels in the ischemic gastrocnemius muscle by proton spectroscopy, as succinate accumulates when the mitochondrial respiratory chain complex II fails to use the FADH2, generated from the conversion of succinate to fumarate in the Krebs cycle. In WT mice, succinate levels accumulated to high levels at six hours after ischemia; by contrast, succinate levels in PHD1$^{-/-}$ muscle did not increase above baseline levels (succinate content: 0.42±0.096 in PHD1$^{-/-}$ versus 0.22±0.048 in WT in baseline conditions; 0.36±0.03 in PHD1$^{-/-}$ versus 1.92±0.58 in WT in ischemia; n=3; P=NS). Biochemical measurements further revealed that the mitochondrial complex I activity in the gastrocnemius muscle was reduced in WT mice but preserved in PHD1$^{-/-}$ mice at six hours after femoral artery ligation.

Ischemia is well known to induce morphological changes reminiscent of mitochondrial myopathies, including the presence of ragged red fibers, identifiable by enhanced histochemical succinate dehydrogenase (SDH) staining.[22] Consistent with our other results that mitochondrial function was better preserved in ischemic PHD1$^{-/-}$ muscle, we found reduced numbers of SDH-positive fibers in PHD1$^{-/-}$ muscle at six hours after onset of ischemia (% SDH-positive fibers/ischemic muscle area: 125±10.3 in PHD1$^{-/-}$ versus 89.2±6.88 in WT mice; n=6; P=0.01). Transmission electron microscopy studies of ischemic gastrocnemius muscle further revealed vacuolization, matrix clarification and disruption of mitochondrial crystae in ischemic WT fibers, while such signs of mitochondrial degeneration were not detectable in PHD1$^{-/-}$ fibers. Taken together, in the absence of PHD1, mitochondrial integrity and performance were better preserved, thereby enabling the ischemic muscle to maintain a critical supply of ATP.

7. Ischemia-Induced Oxidative Stress is Attenuated in Ischemic PHD1$^{-/-}$ Muscle We next sought to determine the mechanisms underlying the mitochondrial protection in ischemic PHD1$^{-/-}$ muscle. Mitochondrial dysfunction in ischemic conditions may result from excessive oxidative stress. We therefore analyzed whether PHD1$^{-/-}$ muscle fibers more efficiently counteracted the oxidative stress. When assessing protein carbonylation as a surrogate marker of the oxidative stress-induced damage by using the oxyblot, we found that ischemia induced considerably more protein oxidation in cytoplasmic or mitochondrial preparations in ischemic WT than PHD1$^{-/-}$ gastrocnemius. Densitometric quantification of the total amount of carbonylated protein revealed that protein oxidation was increased in ischemic WT muscle, but only insignificantly in ischemic PHD1$^{-/-}$ muscle fibers. Use of the ferricytochrome c reduction assay on submitochondrial particle preparations further revealed much higher production levels of reactive superoxide species (ROS) in ischemic WT than PHD1$^{-/-}$ gastrocnemius muscle. Apart from a reduced generation of ROS, the decreased cellular oxidative stress in PHD1$^{-/-}$ muscle could also result from an enhanced antioxidant capacity and superoxide clearance. Indeed, we found that protein levels of the antioxidant enzymes SOD1 and SOD2 (the latter being the most relevant antioxidant mechanism in mitochondria) were significantly higher in the mitochondria of PHD1$^{-/-}$ than WT muscle after ischemia. Upon densitometric quantification, SOD2 levels were increased in ischemic PHD1$^{-/-}$ muscle but only insignificantly in ischemic WT muscle fibers. Thus, in the absence of PHD1, generation of ROS and protein peroxidation were reduced, while ROS clearance was enhanced, resulting in a reduced oxidative stress for the mitochondria with better preservation of mitochondrial function and supply of high energy phosphates after ischemia.

8. PHD1$^{-/-}$ Myoblast Cultures are Protected Against Cellular Stress Conditions The possibility was also considered that the absence of PHD1 might alter the intrinsic property of skeletal myocytes to sustain better hypoxic stress. We therefore cultured PHD1$^{-/-}$ and WT myoblasts and determined cell survival after subjecting them to hypoxia, serum deprivation, or a combination of both stress conditions, to mimic the ischemic situation in vivo. Undifferentiated WT myoblasts detached from the culture dish and died in hypoxic conditions and, even more so, after serum deprivation, or when both stress conditions were combined. In contrast, a larger number of PHD1$^{-/-}$ myoblasts survived the hypoxic or serum-deprivation stress. In order to determine whether this protective effect was cell-autonomous, we analyzed whether conditioned medium of cultured PHD1$^{-/-}$ myoblasts, exposed to oxygen and serum deprivation, could increase the survival of stressed WT cells. Indeed, conditioned medium from PHD1$^{-/-}$ myoblasts enhanced the survival of WT myoblasts after hypoxia and serum deprivation, thus suggesting that a secreted humoral factor(s) provided the protection. Interestingly, conditioned medium from PHD1$^{-/-}$ myoblasts was also capable of reducing the oxidative stress in WT myoblasts.

9. Skeletal Muscle Protection in PHD1$^{-/-}$ Mice is Mediated by HIF-2α

Loss of HIF-2α leads to skeletal myopathy due to mitochondrial dysfunction, indicating that HIF-2α has an important role in mounting an anti-oxidant response.[23] It was therefore evaluated whether HIF-2α might be a downstream target of PHD1, mediating the skeletal muscle resistance to ischemia. Protein expression analysis revealed no genotypic differences in the ischemic induction of HIF1-α in the skeletal muscle of PHD1$^{-/-}$ and WT mice.

By contrast, HIF-2α levels were more elevated in ischemic PHD1$^{-/-}$ than in WT muscle. Additional evidence supporting a predominant role for PHD1 in the regulation of HIF-2α was provided by the accumulation of HIF-2α, but not HIF-1α, in PHD1$^{-/-}$ MEFs (FIG. 1, Panel c). To assess whether ischemic muscle protection in PHD1$^{-/-}$ mice was indeed dependent on HIF-2α, we compared the response to muscle ischemia in viable HIF-2α$^{+/-}$ mice (HIF-2α$^{-/-}$ mice are lethal) and PHD1$^{-/-}$HIF-2α$^{+/-}$ mice (lacking both PHD1 alleles and a single HIF-2α allele), obtained by intercrossing HIF-2α$^{+/-}$ and PHD1$^{-/-}$ mice. PHD1$^{-/-}$HIF-2α$^{+/-}$ mice were healthy, fertile, gained weight normally and had no muscle defects. Similar to WT mice, HIF-2α$^{+/-}$ mice exhibited severe signs of ischemic muscle damage (Table 2). Notably, however, PHD1$^{-/-}$HIF-2α$^{+/-}$ mice, lacking both PHD1 alleles and a single HIF-2α allele, also suffered the same degree of ischemic muscle necrosis as WT mice (Table 2). These genetic findings thus suggest that HIF-2α is a (but, therefore, not the only) critical downstream mediator of the myoprotective activity of PHD1.

10. PHD1 Knock-Down Protects WT Mice Against Ischemic Muscle Damage

Figure 2:
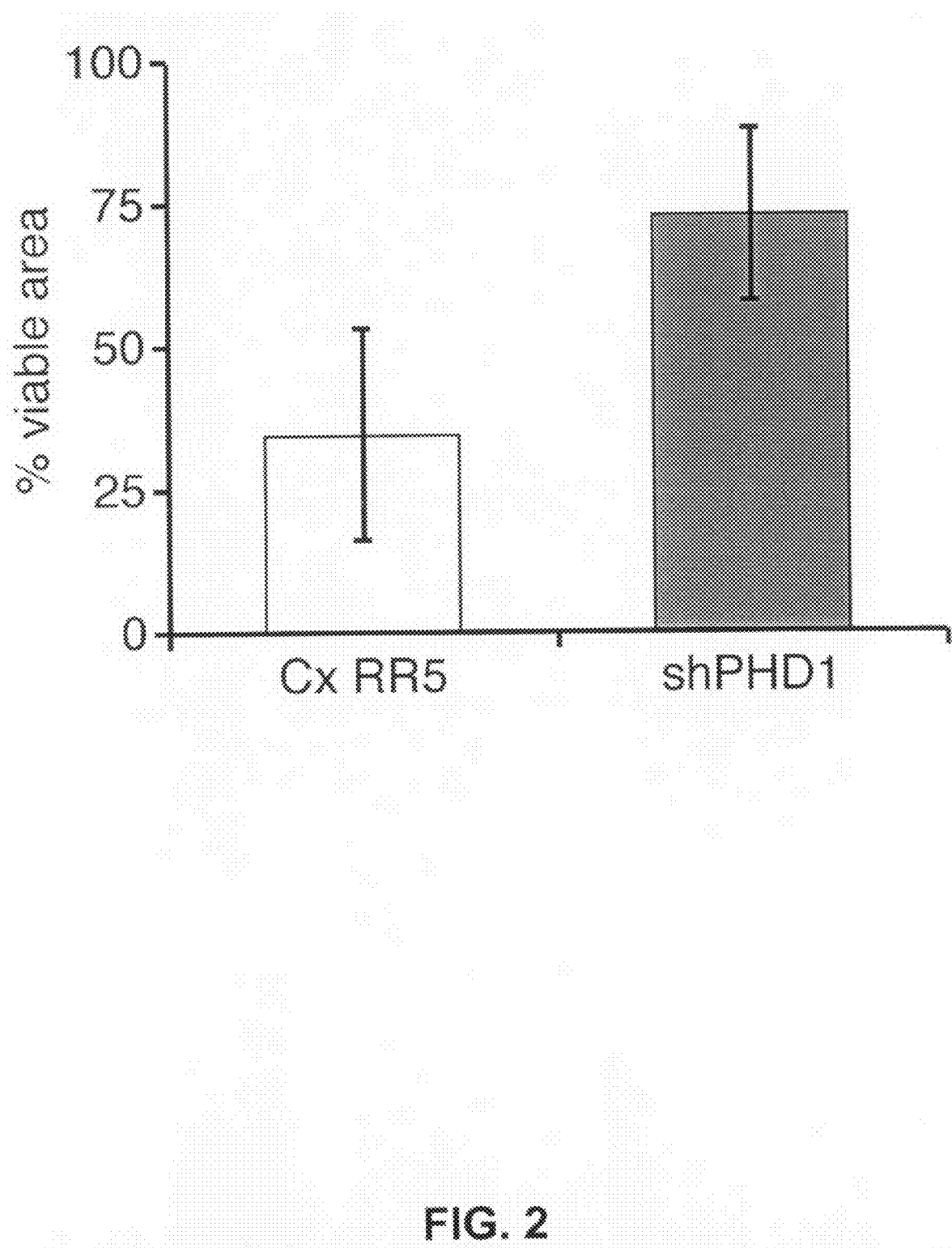
FIG. 2: Therapeutic PHD1-targeting is effective in conditions of acute limb ischemia.

Prompted by our genetic findings that loss of PHD1 prevents ischemic skeletal muscle damage, we sought to determine whether knock-down of PHD1 expression might offer therapeutic opportunities to counteract ischemic fiber injury by using RNAi, previously recognized as an efficient tool to silence gene expression in vivo and in vitro. In order to interfere with endogenous PHD1 expression in skeletal muscle, we transferred PHD1 siRNA in gastrocnemius fibers by using adenovirus-driving transcription of small hairpin PHD1 iRNA (shPHD1iRNA). The short hairpin sequence against PHD1 (5'-CAC CGC TGC ATC ACC TGT ATC TAT TTC TCT TGA AAA TAG ATA CAG GTG ATG CAG C-3' (SEQ ID NO:5)) was cloned into the pAd/block-iT Gateway™ (Invitrogen) vector system according to the manufacturer's instructions. As a control, we used an empty E1-deleted recombinant adenovirus (AdRR5). For viral injection, the leg was depilated at the injection site. After incision of the skin, the gastrocnemius muscle was injected with adenovirus containing shPHD1 or AdRR5 at a volume of 60 µl per muscle, using a Hamilton microsyringe. Ligation of the femoral vessels was performed two days after viral injection, and necrotic tissue areas quantified morphometrically two days after induction of ischemia. RT-PCR analysis revealed that gastrocnemius PHD1 mRNA levels were reduced by 60-80% after intramuscular injection of Adeno-shPHD1iRNA, compared to mice injected with Adenovirus control. In order to increase our chance to abrogate PHD1 expression, we treated PHD1$^{+/-}$ mice. Interestingly, WT and PHD1$^{+/-}$ mice treated three days in advance with sh-PHD1 siRNA showed a significant protection against fiber damage monitored two days after femoral ligation (see FIG. 2). These data show that the inhibition of PHD1 activity is a therapeutic strategy to treat lower limb ischemic diseases as well as to treat pathologies in which muscle degeneration occurs.

In a next step, short hairpin constructs against PHD1 were delivered by electroporation. We used DNA constructs designed to produce short hairpin interference RNA to knock-down PHD1 expression: shPHD1$^{KD}$ (5'-CACCGCTGCAT-CACCTGTATCTATTTCTCTTGAAAATA-GATACAGGTGATGCAGC-3' (SEQ ID NO:6)) and a control shPHD1$^{CTR}$ (5'-CACCGCTTAACCCGTATTGC-CTATTTCTCTTGAAAATAGGCAATACGGGTTAAGC-3' (SEQ ID NO:7)), which differed by a mismatch of ten nucleotides in the PHD1-specific sequence. The efficiency and specificity of shPHD1$^{KD}$ and shPHD1$^{CTR}$ were first tested in cultured murine C2C12 myoblast cells. Compared to non-transfected cells, transfection of C2C12 cells with shPHD1$^{CTR}$ did not affect PHD1 transcript levels (mRNA copies PHD1/10$^3$ mRNA copies β-actin: 12.0±1.0 after vehicle versus 11.3±0.3 after shPHD1$^{CTR}$; n=4; P=n.s.). In contrast, shPHD1$^{KD}$ efficiently lowered PHD1 mRNA levels by 72% (mRNA copies PHD1/10$^3$ mRNA copies β-actin: 3.4±0.5 after shPHD1$^{KD}$; n=4; P<0.05 versus shPHD1$^{CTR}$). shPHD1$^{KD}$ did not knock down PHD2 or PHD3. We then injected and electroporated these constructs into the muscle fibers in vivo, as this method is very efficient and causes negligible muscle damage and inflammation (J. M. McMahon et al., 2001, Gene Ther. 8, 1264-70).

The constructs were electroporated five days prior to the ligation of the femoral artery for two reasons: (i) to achieve sufficient elimination of the pre-existing PHD1 transcripts prior to the induction of ischemia; and (ii) to avoid death of ischemic myofibers before their PHD1 transcript levels would be sufficiently reduced to provide protection. Both the right and left hind limb muscles were electroporated, but only the right femoral artery was ligated, permitting us to use the right legs for histological scoring of muscle necrosis and the left muscles for RNA analysis. To obtain sufficiently low endogenous PHD1 levels after PHD1 knock-down, we used PHD1$^{+/-}$ mice, which only expressed 50% of the PHD1 transcript levels present in WT mice.

Electroporation of shPHD1$^{KD}$ in PHD1$^{+/-}$ muscle reduced PHD1 transcripts to 23±4% (n=13; P<0.001) of the levels normally detected in WT muscle, while a similar dose of shPHD1$^{CTR}$ insignificantly reduced PHD1 levels to 44±5% of WT levels (n=13; P=0.20). Histological analysis at two days after femoral artery ligation revealed that electroporation of shPHD1$^{CTR}$ insignificantly reduced PHD1+/−muscle necrosis (necrotic plantaris muscle area: 5.5±1.2×10$^{-1}$ mm$^2$ in non-electroporated versus 3.7±1.1×10$^{-1}$ mm$^2$ after shPHD1$^{CTR}$; n=13; P=n.s. versus non-electroporated). By contrast, electroporation of shPHD1$^{KD}$ reduced PHD1$^{+/-}$ myofiber necrosis by 83% and 74% as compared to non-electroporated or shPHD1$^{CTR}$-injected muscle, respectively (necrotic plantaris muscle area: 0.9±0.3×10$^{-1}$ mm$^2$ after shPHD1$^{KD}$; n=13; P<0.005 versus non-electroporated and P<0.05 versus shPHD1$^{CTR}$ by t-test and Mann Whitney test). Thus, similar to knock-out of PHD1, knock-down of PHD1 provided protection of myofibers against ischemic necrosis.

Two human shPHD1KD sequences that gave nice knock-down results of PHD1 in human cell lines are: human shPHD1KD-1 (5'-CACCGCTGCATCACCTGTATC-TATTTCTCTTGAAAATAGATACAGGTGATGCAGC-3' (SEQ ID NO:8)), human shPHD1KD-2 (5'-CACCGCCAA-CATCGAGCCACTCTTTTCTCTTGAAAAA-GAGTGGCTCGATGTTGGC-3' (SEQ ID NO:9)). Note that the human shPHD1KD-1 has the same sequence as the mouse shPHD1KD sequence.

We used this sequence for siRNA oligos design. These siRNA oligos were used for in vitro studies in human cell lines and this siRNA PHD1 oligo gave nice results.

11. LNA-Mediated Knock-Down of PHD-1 Expression

Based on the proprietary rules from the Proligo Company, we have designed an antisense LNA to knock down PHD1 in skeletal muscles. This approach can confirm the results obtained in the KO mice, and will allow us to develop a therapeutic approach in order to apply these findings in skeletal muscle degenerative disorders. One example of an LNA that is directed to the murine PHD1 Sequence, coding sequence span from position 284 to position 1543:

```
LNA-Antisense:
                                          (SEQ ID NO: 28)
5' + A + G + G + Ctgagggagg + A + A + G + T 3'

Tm = 71° C.
```

The chosen strategy to deliver the LNA in skeletal muscles is via in vivo electroporation. Skeletal muscle-targeting via in vivo electroporation induces minimal damage of the skeletal muscle fiber and a mild degree of influx of inflammatory cells. We deliver the LNA inside the skeletal muscle fiber just before the limb ischemia protocol during the same anesthetic procedure. Prior to intramuscular injection, mice are anesthetized. The gastrocnemius anterior muscles of anesthetized animals are injected with hyaluronidase two hours prior to injection and electrotransfer of the LNA as is described by McMahon et al., 2001, *Gene Ther.* August; 8(16):1264-70. We perform the experiment on male Sv129 mice, ranging in age from 11 to 18 weeks old. Animals are housed in a disease-free facility with food and water ad libitum. Control experiments with fluorescent scrambled LNA were previously done in order to find the best conditions for the LNA delivery. Forty-eight hours after electroporation, longitudinal sections of gastrocnemius anterior are examined under fluorescent microscope; we chose the condition that shows both homogeneous distribution and high intrafiber fluorescence. The experimental conditions are: 8 µg PHD1-LNA or PHD1$^{SRC}$ LNA was injected in normal saline in a final volume of 25 µl in the gastrocnemius anterior; an electrical field was applied to the muscle immediately. The injection of LNA and the electrotransfer (using a BTX ECM 830 electroporator) are carried out under isofluorane inhalation anesthesia.

Immediately afterwards, limb ischemia is induced as described in materials and methods. The limb ischemia is checked by Doppler analysis six hours after the surgical protocol. Seven days after the electroporation, transverse sections are derived from the gastrocnemius after ischemia; they are subjected to histological and morphometric analysis.

Materials and Methods

1. Gene Inactivation of PHD1, PHD2 and PHD3 Loci

The PHD1 targeting vector contains, from 5' to 3', the following fragments cloned in pKOScramblerNTKV-1908: a 5-Kb KpnI/HindIII fragment located upstream of exon2 as 5' homology; a neo resistance cassette in opposite orientation; a 1.6-Kb BamHI/EcoRV fragment located downstream of exon2 as the 3' homology, and a thymidine kinase selection cassette.

The PHD2 targeting vector contains, from 5' to 3', the following fragments cloned in pPNTLox2: a 5.2-Kb BamHI/HindIII fragment located upstream of exon2 as 5' homology; a neo resistance cassette; a 2.5-Kb XbaI/BamHI fragment located downstream of exon2 as the 3' homology, and a thymidine kinase selection cassette. The PHD3 targeting vector contains, from 5' to 3', the following fragments cloned in pPNTLox2: a 5-Kb KpnI/HindIII fragment located upstream of exon2 as 5' homology; a neo resistance cassette in opposite orientation; a 1.6-Kb BamHI/EcoRV fragment located downstream of exon2 as the 3' homology; and a thymidine kinase selection cassette. ES cells (129 SvEv background) were electroporated with linearized targeting vectors for PHD1, PHD2 or PHD3 as described.[24] Resistant clones were screened for correct homologous recombination by appropriate Southern blot and PCR (see supplemental information). Several PHD1$^{+/-}$, PHD2$^{+/-}$ and PHD3$^{+/-}$ positive clones were obtained. Correctly recombined ES cell clones were aggregated with morula embryos as described[24] to generate chimeric mice that were intercrossed with wild-type Swiss females to obtain get PHD1$^{+/-}$, PHD2$^{+/-}$ and PHD3$^{+/-}$ germline offspring (50% Swiss/50% 129 background). Subsequently, heterozygous breeding pairs were established to generate homozygous PHD1$^{-/-}$, PHD2$^{-/-}$ and PHD3$^{-/-}$ progeny.

2. Quantitative Real Time RT-PCR and Western Blot Analysis

Gene expression was quantified by Real Time RT-PCR, relative to the expression level of alfa-actin, using the following forward (F) and reverse primers (R) and probes (P), labeled with fluorescent dye (FAM or JOE) and quencher (TAMRA).

```
For PHD1:
                                         (SEQ ID NO: 10)
F, 5'-GGTACGTGAGGCATGTTGACAAT-3', (SEQ ID NO: 11)
R, 5'-CTTAACATCCCAGTTCTGATTCAGGTA-3', (SEQ ID NO: 12)
P, 5'-FAM-CCCACGGCGATGGGCGCT-TAMRA-3';

For PHD2:
                                         (SEQ ID NO: 13)
F, 5'-AGTCCCATGAAGTGATCAAGTTCA-3', (SEQ ID NO: 14)
R, 5'-ATCCGCATGATCTGCATGG-3', (SEQ ID NO: 15)
P, 5'-FAM-TGCCCACGTCAGAGAGCAACATCAC-TAMRA-3';

For PHD3,
                                         (SEQ ID NO: 16)
F, 5'-TTATCAGACTGAAGAGCTACTGTAATGATC-3', (SEQ ID NO: 17)
R, 5'-TTACCAGTGTCAATTATATCTTCAACAATC-3', (SEQ ID NO: 18)
P, 5'-JOE-TGAGAGATCATCTCCACCAATAACTTTATGTCCC-
TAMRA-3';

For Glut1,
                                         (SEQ ID NO: 19)
F, 5'-GGGCATGTGCTTCCAGTATGT-3', (SEQ ID NO: 20)
R, 5'-ACGAGGAGCACCGTGAAGAT-3', (SEQ ID NO: 21)
P, 5'-JOE-CAACTGTGCGGCCCCTACGTCTTC-TAMRA-3';

For Glut4,
                                         (SEQ ID NO: 22)
F, 5'-GATCTGCCGCTCCGAAAAG-3', (SEQ ID NO: 23)
R, GGAAGTCTCTCCCACGGTGA-3', (SEQ ID NO: 24)
P, 5'-JOE-TACCAAGCCTCCCAGCCCTTACGCT-TAMRA-3';

For α-actin,
                                         (SEQ ID NO: 25)
F, 5'-AGAGGGAAATCGTGCGTGAC-3', (SEQ ID NO: 26)
R, 5'-CAATAGTGATGACCTGGCCGT-3'

(SEQ ID NO: 27)
P, 5'-JOE-CACTGCCGCATCCTCTTCCTCCC-TAMRA-3'.
```

For Western blot analysis, gastrocnemius samples were homogenized on ice using lysis buffer (8 M urea, 1/10 v/v glycerol, 1/20 v/v 20% SDS, 1/200 v/v 1 M DTT, 1/100 v/v 0.5 M Tris (pH 6.8)) containing a cocktail of protease inhibitors (Complete Mini, Roche). Then samples were centrifuged 13,000 rpm at 4° C. and supernatants were collected. Protein concentration was determined and 100 µg were fractionated by SDS-PAGE electrophoresis and transferred onto nitrocellulose membranes (Hybond-ECL, Amersham Biosciences). Membranes were incubated with specific antibodies against PHD1, PHD2, PHD3, HIF-1α (Novus Biologicals, Littleton, USA), HIF-2α (Novus Biologicals), Glut-1 (Alpha Diagnostic International, San Antonio, USA) and Glut-4 (Alpha Diagnostic International). Bound primary antibody was visualized with species-specific horseradish peroxidase-conjugated secondary antibody (Dakocytomation) and chemiluminescence system (Pierce).

3. Mouse Model of Limb Ischemia

Limb ischemia was induced by high unilateral right or bilateral ligation of the femoral artery and vein, and of the cutaneous vessels branching from the caudal femoral artery, sparing the femoral nerve. Crural muscles were dissected and processed for histological analysis two days or seven days after ligation. For assessment of re-vascularization, bismuth gelatino-angiography was carried out, and arterioles branching directly from pre-existing collaterals, connecting the femoral and saphenous artery in the adductor region of the thigh, were quantified by morphometry as described on histological cross sections after seven days.[25] Side branches were categorized as second or third generation according to their luminal area (>300 μm, <300 μm, respectively). For micro-CT angiography, hind limbs were perfused with a solution containing 30% barium and 5% gelatin, dissected in toto, and the crural vasculature was imaged using a high-resolution micro-CT imaging system (SkyScan-1172, SkyScan, Aartselaar, Belgium), with a voltage of 50 kVp and a current of 200 μA. Three-dimensional morphometric analysis was performed to assess vessel volume, number, and thickness in a volume of interest (VOI) defined as the calf area. Blood flow in non-operated and ligated limbs was measured applying 15 μm fluorescent microspheres ($1 \times 10^6$ beads per ml, Molecular Probes, Eugene, Oreg.) after maximal vasodilation with sodium nitroprusside (50 ng/ml, Sigma) as described.[26,27]

4. Histology, Immunostaining and Morphometry

For immunostaining, the crural flexor muscle group was dissected, fixed in 4% PFA, dehydrated, embedded in paraffin, and sectioned at a 10 μm thickness. Briefly, after deparaffinization and rehydration, sections were digested with 0.2% trypsin (Sigma), blocked, and incubated overnight with a rat anti-mouse CD31 antibody (BD Pharmingen; dilution 1/500), a rabbit anti-desmin antibody (Abcam; dilution 1/100), an anti-PHD1 antibody or with an anti-Glut4 antibody (Alpha Diagnostic International). Sections were subsequently incubated with appropriate secondary antibodies, developed with 3,3'-diaminobenzidine (DAB, Sigma) as a chromogen substrate and counterstained with Harris Hematoxilin. For detection of hypoxic cells, mice were treated with pimonidazole (Chemicon) one hour prior to dissection of muscle specimens, and staining with the Hydroxyprobe-1 antibody (Chemicon) was carried out according to the manufacturer's instructions. Microscopic analysis was performed with a Zeiss Axioplan 2 imaging microscope, equipped with an Axiocam HrC camera and KS300 morphometry software (Zeiss). Capillary density, fiber size, and the cross-sectional area of viable and necrotic zones were quantified on eight entire sections (each 320 μm apart) of the crural muscle package. For assessment of metabolic fiber properties, consecutive cryostat sections (12 μm) of snap frozen crural muscles were subjected to histochemical SDH (succinate dehydrogenase, reveals oxidative vs. non-oxidative fibers), glycogen phosphorylase (reveals glycogenolytic potential), and myofibrillar ATPase stainings (pH 4.1; reveals slow versus fast fibers) according to standard protocols. PAS staining was carried out to assess glycogen content.

5. In Vivo and In Vitro MRS Measurements

In vivo $^{31}$phosphorus MRS experiments on lower limbs were performed at 188 MHz in a Bruker Biospec (Karlsruhe, Germany), equipped with a horizontal 4.7 Tesla superconducting magnet with 30 cm bore, using a 10 mm transmit-receive surface coil. Prior to the measurement, the mice were anesthetized with intraperitoneally (i.p.) injected sodium pentobarbital (1 lg body weight Nembutal, Sanofi, Belgium). Mice were placed on a Perspex plate such that lower limbs was positioned directly inside the circular surface coil. Serial $^{31}$phosphorus NMR spectra were acquired every 13 minutes during 20 minutes to two hours (90 degree pulse of 11 seconds, total repetition time (TR)=0.75 seconds, number of averages (NA)=1024, spectral width=27 kHz; acquisition size=2048 points; no proton decoupling). The signals for Pcr, Pi, ATP resonances were processed by zero-filling to 4096 points and exponential multiplication of 6 Hz. During the in vivo $^{31}$phosphorus MRS measurements, the body temperature of the mice was kept at 36° C. with the use of warm air ventilation in the magnet bore. In vitro analysis of gastrocnemius extracts from operated limbs in WT and PHD1−/− mice were performed in a high resolution AMX 360 (8.4 Tesla) spectrometer (Bruker, Karlsruhe, Germany). Specific settings for the tissue extracts (278 K) were, TR=2.5 seconds, NA=3072 or 12288, 1 H WALTZ-16-decoupling during the one-second acquisition; and for the lysates (295 K), TR=2.5 seconds, NA=256, no proton decoupling. The tissue extracts were measured at 278 K to exploit the substantially shorter relaxation time at low temperature (typically a factor three).[28] Absolute lactate concentrations were determined using a phantom sample of 5-FU in water (2.8 mM, 500 l) with a coaxial FBA reference sample insert.

6. Myoblast Isolation and Cellular Treatment

Purification of the primary muscle-derived cells was performed using a previously described protocol.[29] The hind limbs were removed from WT or PHD1$^{-/-}$ mice, and the bone was dissected. The remaining muscle mass was minced into a coarse slurry using razor blades. Cells were enzymatically dissociated by adding 0.2% collagenase-type B for 45 minutes at 37° C., dispase (grade II, 2.4 U/ml) for 30 minutes. The muscle cell extract was preplated on collagen-coated flasks. We isolated different populations of muscle-derived cells based on the number of preplates performed on collagen-coated flasks. Preplate (PP) 1 represented a population of muscle-derived cells that adhered in the first hour after isolation, PP2 in the next two hours, PP3 in the next 18 hours, and the subsequent preplates were obtained at 24-hour intervals (PPs 4-6). The myogenic population in each flask was evaluated by desmin staining and on differentiation ability when cultured in a fusion medium. The proliferation medium was F12-Ham-supplemented with 20% FBS (growth medium, GM) and 1% penicillin/streptomycin; the fusion medium was F12-Ham supplemented with 2% HS and 1% antibiotic solution (penicillin/streptomycin) (differentiation medium, DM). All the culture medium supplies were purchased through Gibco® Cell Culture Products (Invitrogen, Merelbeke, Belgium).

For cellular treatment, cells seeded at 10,000 cells/cm$^2$ were grown in 48-well plates and exposed either to normoxia or hypoxia in GM or in serum-deprived medium during 24, 48 or 72 hours. Hypoxia was induced by placing the culture plates into a 37° C. incubator in a humidified atmosphere perfused with 95% $N_2$/5% $CO_2$. Serum deprivation was induced by replacing the GM by serum-free F12-Ham. The oxygen level was 2%. Co-cultures of WT myogenic cells and PHD1$^{-/-}$ myogenic cells were done after fluorescent labeling of each cell type with CellTracker™ Red CMTPX for WT cells and CellTracker™ Green CMFDA (5-chloromethylfluorescein diacetate) for PHD1$^{-/-}$ cells (Molecular Probes™, Invitrogen, Merelbeke, Belgium). In direct co-cultures, survival and growth of each cell type (5000 cells/cm$^2$ each) were monitored by numeration of fluorescent cells under microscope (only attached cells are considered as alive). In indirect co-cultures, PHD1$^{-/-}$ cells were seeded in inserts (0.4-μm diameter pores; Falcon™, BD Biosciences) placed over the WT cell-containing wells.

7. Design of Short Hairpin (sh)RNAs

Using online shRNA oligo sequence selector tool (Invitrogen RNAi Designer), shRNA templates were designed to match non-conserved nucleotide sequences within the mouse PHD1 targeting sequence (GenBank accession no. NM_053208). The sequences of the oligonucleotides are designed to use them in the pENTR™/U6 vector (Invitrogen), a vector that allows efficient transient expression of short hairpin RNA (shRNA) or stable expression of shRNA following recombination with a suitable destination vector in mammalian cells. The shRNA oligos were chemically synthesized by Invitrogen. The shRNAs design was based on a 21 nucleotide sense sequence derived from the target gene, followed by a short spacer of 9 nucleotides (i.e. loop) and a 21 nucleotide sequence that is the reverse complement of the initial target sequence. The three sets of shRNAs PHD1 targeting sequences correspond to the coding region: 1224-1244 (GCT GCA TCA CCT GTA TCT ATT (SEQ ID NO:29)), 1319-1339 (GCC AAC ATC GAG CCA CTC TTT (SEQ ID NO:30)) and 1490-1510 (GGT GTT CAA GTA CCA GTA TCA (SEQ ID NO:31)) relative to the start codon. A mutated version was designed (mutated sequence) to be used as negative control.

The three shPHD1 were cloned into the pENTR™/U6 vector according to the manufacturer's instructions. The orientations of the short hairpins were confirmed by sequencing. Efficiency of shPHD1_pENTR™/6 vectors was tested by transfection into mouse embryonic fibroblasts (MEFs), embryonic Stem (ES) cells and mouse myoblast cell line (C2C12). Cells were transfected with 5 μg shPHD1_pENTR™/U6 plasmid or GFP-plasmid (as control) by using Fugene 6 (Roche), according to the manufacturer's instructions. After 48 hours, cells were lysed and decline in PHD1 RNA expression was referred to percentage of GPF positive cells.

shPHD1 cassettes were transferred from pENTR™/U6 plasmid to pLenti6/BLOCK-iT-DEST expression plasmid for lentiviral production that was done as described.[30] Briefly, 3 μg of lentiviral vector (pLenti6/BLOCK-iT-DEST shPHD1 expression plasmid) and 9 μg ViraPower™ Packaging Mix were mixed in Opti-MEM I medium according to the manufacturer's instructions (Invitrogen). Packaging Mix and lentiviral vector were co-transfected in 293FT cells by using the Lipofectamine™ 2000 transfection reagent (Invitrogen). Virus-containing supernatans was collected 48 to 72 hours post-transfection, filtered through a 0.22 μm filter, and used for infection.

Infection protocol. Alternatively, skeletal muscle fibers were transfected with shPHD1_pENTR™/U6 plasmid by in vivo electroporation.

8. Delivery of Plasmids to Skeletal Muscle

The shPHD1 pENTR™/U6 plasmids were delivered to the skeletal muscle of PHD1$^{+/-}$ mice via in vivo electroporation, a procedure that induces only minimal fiber damage and inflammation. EP was carried out five days prior to induction of limb ischemia as follows. The crural muscles of anesthetized animals were injected with hyaluronidase enzyme (60 μl; 0.4 U/μl) one hour prior to plasmid injection. Thereafter, 40 μg of shPHD1$^{KD}$ or shPHD1$^{CTR}$ pENTR™/U6 plasmid (final volume: 30 μl in normal saline) was injected in the crural muscles. Injected muscles were immediately electroporated with a strain of eight pulses (120V; duration 20 ms; intervals 1/second), using an electroporation system (BTX ECM 830 electroporator; Genetronix, Inc.) with Tweezertrode circular electrodes (diameter 7 mm). Induction of hind limb ischemia, analysis of muscle necrosis and RNA analysis were performed as described above.

9. Statistical Methods

The data are represented as mean±S.E.M. of the indicated number of measurements. Standard t-tests were used to calculate significance levels between groups. ANOVA Univariate analysis was used to correct p-values for multiple comparisons against a single wild-type group (Dunnett's correction for multiple testing) or against various groups (Bonferroni correction for multiple testing). In the hind limb ischemia model, muscle necrosis was absent in some of the PHD1$^{-/-}$ or shPHD1$^{KD}$ mice (indicative of complete protection against muscle damage), thereby disturbing normal Gaussian distribution as calculated by Shapiro-Wilk tests. In these cases, we used non-parametrical Mann-Whitney tests to calculate statistical significance between these groups. The P-values obtained by ANOVA remained significant when correcting for the total muscle area analyzed. SPSS (Statistical Software Package version 11.0 for Mac OS X) was used for all these calculations.

TABLES

TABLE 1

Inheritance and viability of mice deficient for PHD1, PHD2 and PHD3.

|  | +/+ | +/− | −/− |
|---|---|---|---|
| PHD1 | 28 (21%) | 78 (58%) | 29 (22%) |
| PHD3 | 57 (31%) | 95 (51%) | 34 (18%) |
| PHD2 | 126 (38%) | 205 (62%) | 0 (0%) |

Data represent total numbers and percentage of viable mice showing the indicated genotype at birth.

TABLE 2

Ischemic tissue damage in PHD1$^{-/-}$, PHD3$^{-/-}$ and PHD2$^{+/-}$ mice.

|  | PHD1$^{-/-}$ | PHD3$^{-/-}$ | PHD1$^{-/-}$ HIF-2α$^{+/-}$ | WT |
|---|---|---|---|---|
| Viable muscle fiber area (%) | 87.2$^{\#,\,*}$ ± 7.03 | 51.2 ± 11.5 | 55.9 ± 25.2 | 50.4 ± 13.7 |

Data represent mean ± SEM percentage of the absolute transverse section area of the gastrocnemius muscle occupied by healthy and viable muscle fibers seven days after arterial ligation.
n = 12 limbs;
$^{\#}$P = 0.026 vs WT;
*P = 0.014 vs PHD3$^{+/-}$.

REFERENCES

1. Semenza G. L. HIF-1 and tumor progression: pathophysiology and therapeutics. *Trends Mol. Med.* 8:S62-7 (2002).
2. Pugh C. W. and P. J. Ratcliffe. Regulation of angiogenesis by hypoxia: role of the HIF system. *Nat. Med.* 9:677-84 (2003).
3. Wiesener M. S. and P. H. Maxwell. HIF and oxygen sensing: as important to life as the air we breathe? *Ann. Med.* 35:183-90 (2003).
4. Maynard M. A. et al. Multiple splice variants of the human HIF-3α locus are targets of the von Hippel-Lindau E3 ubiquitin ligase complex. *J. Biol. Chem.* 278:11032-40 (2003).

5. Tian H., S. L. McKnight, and D. W. Russell. Endothelial PAS domain protein 1 (EPAS1), a transcription factor selectively expressed in endothelial cells. *Genes Dev.* 11:72-82 (1997).
6. Wang G. L., B. H. Jiang, E. A. Rue, and G. L. Semenza. Hypoxia-inducible factor 1 is a basic-helix-loop-helix-PAS heterodimer regulated by cellular O2 tension. *Proc. Natl. Acad. Sci. U.S.A.* 92:5510-4 (1995).
7. Huang L. E., Z. Arany, D. M. Livingston, and H. F. Bunn. Activation of hypoxia-inducible transcription factor depends primarily upon redox-sensitive stabilization of its alpha subunit. *J. Biol. Chem.* 271:32253-9 (1996).
8. Ohh M. et al. Ubiquitination of hypoxia-inducible factor requires direct binding to the beta-domain of the von Hippel-Lindau protein. *Nat. Cell Biol.* 2:423-7 (2000).
9. Maxwell P. H. et al. The tumor suppressor protein VHL targets hypoxia-inducible factors for oxygen-dependent proteolysis. *Nature* 399:271-5 (1999).
10. Krek W. VHL takes HIF's breath away. *Nat. Cell Biol.* 2:E121-3 (2000).
11. Wiesener M. S. et al. Induction of endothelial PAS domain protein-1 by hypoxia: characterization and comparison with hypoxia-inducible factor-1α. *Blood* 92:2260-8 (1998).
12. Ivan M. et al. HIFα targeted for VHL-mediated destruction by proline hydroxylation: implications for O2 sensing. *Science* 292:464-8 (2001).
13. Jaakkola P. et al. Targeting of HIF-α to the von Hippel-Lindau ubiquitylation complex by O2-regulated prolyl hydroxylation. *Science* 292:468-72 (2001).
14. Masson N., C. Willam, P. H. Maxwell, C. W. Pugh, and P. J. Ratcliffe. Independent function of two destruction domains in hypoxia-inducible factor-alpha chains activated by prolyl hydroxylation. *Embo. J.* 20:5197-206 (2001).
15. Epstein A. C. et al. *C. elegans* EGL-9 and mammalian homologs define a family of dioxygenases that regulate HIF by prolyl hydroxylation. *Cell* 107:43-54 (2001).
16. Bruick R. K. and S. L. McKnight. A conserved family of prolyl-4-hydroxylases that modify HIF. *Science* 294:1337-40 (2001).
17. Hofer T., I. Desbaillets, G. Hopfl, R. H. Wenger, and M. Gassmann. Characterization of HIF-1α overexpressing HeLa cells and implications for gene therapy. *Comp. Biochem. Physiol. C. Toxicol. Pharmacol.* 133:475-81 (2002).
18. Berra E. et al. HIF prolyl-hydroxylase 2 is the key oxygen sensor setting low steady-state levels of HIF-1α in normoxia. *Embo. J.* 22:4082-90 (2003).
19. Appelhoff R. J. et al. Differential function of the prolyl hydroxylases PHD1, PHD2, and PHD3 in the regulation of hypoxia-inducible factor. *J. Biol. Chem.* 279:38458-65 (2004).
20. Elson D. A. et al. Induction of hypervascularity without leakage or inflammation in transgenic mice overexpressing hypoxia-inducible factor-1 alpha. *Genes Dev.* 15:2520-32 (2001).
21. Willam C. et al. Peptide blockade of HIFα degradation modulates cellular metabolism and angiogenesis. *Proc. Natl. Acad. Sci. U.S.A.* 99:10423-8 (2002).
22. Heffner R. R. and S. A. Barron. The early effects of ischemia upon skeletal muscle mitochondria. *J. Neurol. Sci.* 38:295-315 (1978).
23. Scortegagna M. et al. Multiple organ pathology, metabolic abnormalities and impaired homeostasis of reactive oxygen species in Epas1−/− mice. *Nat. Genet.* 35:331-40 (2003).
24. Stalmans I. et al. Arteriolar and venular patterning in retinas of mice selectively expressing VEGF isoforms. *J. Clin. Invest.* 109:327-36 (2002).
25. Carmeliet P. et al. Synergism between vascular endothelial growth factor and placental growth factor contributes to angiogenesis and plasma extravasation in pathological conditions. *Nat. Med.* 7:575-83 (2001).
26. Kobayashi N., K. Kobayashi, K. Kouno, S. Horinaka, and S. Yagi. Effects of intra-atrial injection of colored microspheres on systemic hemodynamics and regional blood flow in rats. *Am. J. Physiol.* 266:H1910-7 (1994).
27. Luttun A. et al. Revascularization of ischemic tissues by PlGF treatment, and inhibition of tumor angiogenesis, arthritis and atherosclerosis by anti-Flt1. *Nat. Med.* 8:831-40 (2002).
28. Kamm V. J. et al. Effect of modulators on 5-fluorouracil metabolite patterns in murine colon carcinoma determined by in vitro 19F nuclear magnetic resonance spectroscopy. *Cancer Res.* 54:4321-6 (1994).
29. Rando T. A. and H. M. Blau. Primary mouse myoblast purification, characterization, and transplantation for cell-mediated gene therapy. *J. Cell Biol.* 125:1275-87 (1994).
30. Rubinson D. A. et al. A lentivirus-based system to functionally silence genes in primary mammalian cells, stem cells and transgenic mice by RNA interference. *Nat. Genet.* 33:401-6 (2003).

What is claimed is:

1. A method of reducing and/or to treating skeletal muscle cell degeneration in a subject in need thereof, the method comprising:

administering to skeletal muscle of the subject a molecule selected from the group consisting of a ribozyme against nucleic acids encoding PHD-1, a short interfering RNA (siRNA) hybridizing with RNA molecules encoding PHD-1, a locked nucleic acid hybridizing with RNA molecules encoding PHD-1, and any combination thereof, so as to reduce and/or to treat skeletal muscle degeneration in the subject.

2. The method according to claim 1, wherein said skeletal muscle cell degeneration is due to ischemia, ischemia resulting from chronic pulmonary disease (COPD), and/or critical limb ischemia.

3. The method according to claim 1, wherein said skeletal muscle cell degeneration is due to a reduced glycolytic rate.

4. The method according to claim 1, wherein said skeletal muscle cell degeneration is due to immobilization.

5. The method according to claim 1, wherein said skeletal muscle cell degeneration is due to muscle denervation.

6. The method according to claim 1, wherein said skeletal muscle cell degeneration is due to a muscle dystrophy.

* * * * *

```
                        SEQUENCE LISTING

<160> NUMBER OF SEQ ID NOS: 31

<210> SEQ ID NO 1
<211> LENGTH: 2111
<212> TYPE: DNA
<213> ORGANISM: Homo sapiens

<400> SEQUENCE: 1
gctttcccct gcctgcctgt ctctagtttc tctcacatcc cttttttttt ttcctttctc      60
tagccaccct gaagggtccc ttcccaagcc cttagggacc gcagaggact tggggaccag    120
caagcaaccc ccagggcacg agaagagctc ttgctgtctg ccctgcctca ccctgcccca    180
cgccaggccc ggtggccccc agctgcatca agtggaggcg gaggaggagg cggaggaggg    240
```

-continued

```
tggcaccatg ggcccgggcg gtgccctcca tgcccggggg atgaagacac tgctgccatg      300
gacagcccgt gccagccgca gcccctaagt caggctctcc ctcagttacc agggtcttcg      360
tcagagccct tggagcctga gcctggccgg gccaggatgg gagtggagag ttacctgccc      420
tgtcccctgc tcccctccta ccactgtcca ggagtgccta gtgaggcctc gcagggagt      480 gggaccccca gagccacagc cacctctacc actgccagcc ctcttcggga cggttttggc      540
gggcaggatg gtggtgagct gcggccgctg cagagtgaag gcgctgcagc gctggtcacc      600 aagggggtgcc agcgattggc agcccagggc gcacggcctg aggcccccaa acggaaatgg      660
gccgaggatg gtggggatgc cccttcaccc agcaaacggc cctgggccag gcaagagaac      720
caggaggcag agcgggaggg tggcatgagc tgcagctgca gcagtggcag tggtgaggcc      780
agtgctgggc tgatggagga ggcgctgccc tctgcgcccg agcgcctggc cctggactat      840
atcgtgccct gcatgcggta ctacggcatc tgcgtcaagg acagcttcct gggggcagca      900
ctgggcggtc gcgtgctggc cgaggtggag gccctcaaac ggggtgggcg cctgcgagac      960
gggcagctag tgagccagag ggcgatcccc ccgcgcagca tccgtgggga ccagattgcc     1020
tgggtggaag gccatgaacc aggctgtcga agcattggtg ccctcatggc ccatgtggac     1080
gccgtcatcc gccactgcgc agggcggctg ggcagctatg tcatcaacgg cgcaccaag      1140 gccatggtgg cgtgttaccc aggcaacggg ctcgggtacg taaggcacgt tgacaatccc     1200
cacggcgatg ggcgctgcat cacctgtatc tattacctga atcagaactg ggacgttaag     1260
gtgcatggcg gcctgctgca gatcttccct gagggccggc ccgtggtagc caacatcgag     1320
ccactctttg accggttgct cattttctgg tctgaccggc ggaaccccca cgaggtgaag     1380
ccagcctatg ccaccaggta cgccatcact gtctggtatt ttgatgccaa ggagcgggca     1440
gcagccaaag acaagtatca gctagcatca ggacagaaag gtgtccaagt acctgtatca     1500
cagccgccta cgcccaccta gtggccagtc cagagccgc atggcagaca gcttaaatga     1560
cttcaggaga gccctgggcc tgtgctggct gctccttccc tgccaccgct gctgcttctg     1620
actttgcctc tgtcctgcct ggtgtggagg ctctgtctg ttgctgagga ccaaggagga     1680
gaagagacct tgctgccccc atcatggggg ctggggttgt cacctggaca ggggcagcc     1740 gtggaggcca ccgttaccaa ctgaagctgg ggcctgggt cctaccctgt ctggtcatga     1800
ccccattagg tatggagagc tgggaggagg cattgtcact tcccaccagg atgcaggact     1860 tgggggttgag gtgagtcatg gcctcttgct ggcaatgggg tggaggagt accccccaagt     1920 cctctcactc ctccagcctg gaatgtgaag tgactcccca acccctttgg ccatggcagg     1980 cacctttttgg actgggctgc cactgcttgg gcagagtaaa aggtgccagg aggagcatgg     2040
gtgtggaagt cctgtcagcc aagaaataaa agtttacctc agagctgcaa aaaaaaaaa     2100 aaaaaaaaa a                                                          2111
```

<210> SEQ ID NO 2
<211> LENGTH: 407
<212> TYPE: PRT
<213> ORGANISM: Homo sapiens

<400> SEQUENCE: 2

Met Asp Ser Pro Cys Gln Pro Gln Pro Leu Ser Gln Ala Leu Pro Gln
1               5                   10                  15

Leu Pro Gly Ser Ser Glu Pro Leu Glu Pro Glu Pro Gly Arg Ala
            20                  25                  30

Arg Met Gly Val Glu Ser Tyr Leu Pro Cys Pro Leu Leu Pro Ser Tyr
        35                  40                  45

His Cys Pro Gly Val Pro Ser Glu Ala Ser Ala Gly Ser Gly Thr Pro
    50                  55                  60

Arg Ala Thr Ala Thr Ser Thr Thr Ala Ser Pro Leu Arg Asp Gly Phe
65                  70                  75                  80

Gly Gly Gln Asp Gly Gly Glu Leu Arg Pro Leu Gln Ser Glu Gly Ala
                85                  90                  95

Ala Ala Leu Val Thr Lys Gly Cys Gln Arg Leu Ala Ala Gln Gly Ala
            100                 105                 110

Arg Pro Glu Ala Pro Lys Arg Lys Trp Ala Glu Asp Gly Gly Asp Ala
        115                 120                 125

Pro Ser Pro Ser Lys Arg Pro Trp Ala Arg Gln Glu Asn Gln Glu Ala
    130                 135                 140

Glu Arg Glu Gly Gly Met Ser Cys Ser Cys Ser Ser Gly Ser Gly Glu
145                 150                 155                 160

Ala Ser Ala Gly Leu Met Glu Ala Leu Pro Ser Ala Pro Glu Arg
                165                 170                 175

Leu Ala Leu Asp Tyr Ile Val Pro Cys Met Arg Tyr Tyr Gly Ile Cys
            180                 185                 190

Val Lys Asp Ser Phe Leu Gly Ala Ala Leu Gly Gly Arg Val Leu Ala
        195                 200                 205

Glu Val Glu Ala Leu Lys Arg Gly Gly Arg Leu Arg Asp Gly Gln Leu
    210                 215                 220

Val Ser Gln Arg Ala Ile Pro Pro Arg Ser Ile Arg Gly Asp Gln Ile
225                 230                 235                 240

Ala Trp Val Glu Gly His Glu Pro Gly Cys Arg Ser Ile Gly Ala Leu
                245                 250                 255

Met Ala His Val Asp Ala Val Ile Arg His Cys Ala Gly Arg Leu Gly
            260                 265                 270

Ser Tyr Val Ile Asn Gly Arg Thr Lys Ala Met Val Ala Cys Tyr Pro
        275                 280                 285

Gly Asn Gly Leu Gly Tyr Val Arg His Val Asp Asn Pro His Gly Asp
    290                 295                 300

Gly Arg Cys Ile Thr Cys Ile Tyr Tyr Leu Asn Gln Asn Trp Asp Val
305                 310                 315                 320

Lys Val His Gly Gly Leu Leu Gln Ile Phe Pro Glu Gly Arg Pro Val
                325                 330                 335

Val Ala Asn Ile Glu Pro Leu Phe Asp Arg Leu Leu Ile Phe Trp Ser
            340                 345                 350

Asp Arg Arg Asn Pro His Glu Val Lys Pro Ala Tyr Ala Thr Arg Tyr
        355                 360                 365

Ala Ile Thr Val Trp Tyr Phe Asp Ala Lys Glu Arg Ala Ala Ala Lys
370                 375                 380

Asp Lys Tyr Gln Leu Ala Ser Gly Gln Lys Gly Val Gln Val Pro Val
385                 390                 395                 400

Ser Gln Pro Pro Thr Pro Thr
                405

<210> SEQ ID NO 3
<211> LENGTH: 2034
<212> TYPE: DNA
<213> ORGANISM: Mus musculus

<400> SEQUENCE: 3

```
ccacgcgtcc gggcggcgcc gaggccggag gaaaaagctc gccaccccca tcagtccctt      60
ctcaagctcc tagagacaac tgtggacttg gggaccagcg agcaccccca gagcactaga     120 ggagccctg  ctgcctgccc tgcctcaccc tgccccacac gaggcccagc ggcccggggc     180
tgcatcaagt ggaggaggag gaggcggagg agggtggcac catgggcccg gccgtgccc     240 tccatgcccg ggggatgaag acactgctgc catggacagc ccgtgccagc cgcaggccct     300
gaatcaagct ctccctcagt tgccagggtc tgtgtcagag tccttggagt ctagccgagc     360
cagaatgggg gtggagagtt acctgccctg ccctctgctc ccggcctatc accgtccagg     420
agcatctggg gaggcctcgg ctggcaatgg acccccaga accacagcca ctgctactac     480
gaccactgcc agtccctgc  gggagggctt tggtgggcag gatggtggtg agctttggcc     540
actgcagagt gaaggtgctg ctgcgttggt caccaaggag tgccagcgac tggcggccca     600
gggtgcccgg cctgaggccc ccaaacggaa gtgggccaag gatggtgggg atgccccttc     660
acccagcaag cgaccgtggg ccaggcaaga gaaccaggag gccaaggggg aaagtggtat     720
gggctgtgac agcggtgcca gcaacagcag cagcagcagc agcaacacta ccagtagcag     780
tggcgaggca agtgctaggc tgagggagga agtccagccc tctgcacctg agcgcctggc     840
cctggactat attgtgcctt gcatgcggta ctatggtatc tgtgtcaagg acaacttctt     900
gggggcagta ctgggtggcc gtgtgctggc tgaggtggaa gccctgaagt ggggcgggcg     960
tcttcgtgat gggcaactag tgagccagcg ggcgatccca ccgcgcagca ttcgtgggga    1020
ccagattgcc tgggtagaag gtcacgagcc aggctgccgg agcattggtg ccctcatggc    1080
tcacgtggac gcagtaatcc gccactgtgc agggcggctg ggcaactacg tcatcaatgg    1140
gcgcaccaag gccatggtgg cgtgttatcc aggcaatggg ctcgggtacg tgaggcatgt    1200
tgacaatccc cacggcgatg ggcgctgcat cacctgtatc tattacctga atcagaactg    1260
ggatgttaag gtgcatggcg gcctgctgca gatcttcccc gagggtcggc cagtggtagc    1320
caacatcgag ccactctttg accggttgct cattttctgg tctgaccgac ggaacccaca    1380
tgaggtgaag ccagcctatg ccaccaggta cgccatcact gtctggtatt ttgatgccaa    1440
ggaacgggca gcagccagag acaagtatca gctagcatcg ggacagaaag tgttcaagt     1500 accagtatca cagccaacta cacctaccta atggccagcc ccagagctgc gtggaccagc    1560
agcagctcct gcctcagtgc ccgctccttt cctgccactg ctgctgcttc tggcttgcct    1620
ctgtactgtg tggtgtggag ggcactaagt atcactgagg agcaacaagg agagacctct    1680
gctgccccgt gagcgagcgg tgctgggttt tgacctgggc agtggccagt gtggctggcg    1740
gtcatgactg gtggctgtgt ctggtccgtt gagtgtagag ctgagaagag gcaggatttg    1800
gggttgaggt gagtcatggc ctcttgctgg aaaggtgtgt tggggtgtgg gtgtcatctc    1860
accctcgtcc ccactcctcc ggcctggaat gtgaagtgac tccccagccc ctttggctgt    1920
ggcagtgtat ggactgggct gccactgtct gggcagagta gggtgccatg acgagcatgg    1980
gtatggaggt tctgccagcc aagaaataaa agtttacctc agagctgcaa aaaa          2034
```

<210> SEQ ID NO 4
<211> LENGTH: 419
<212> TYPE: PRT
<213> ORGANISM: Mus musculus

<400> SEQUENCE: 4

Met Asp Ser Pro Cys Gln Pro Gln Ala Leu Asn Gln Ala Leu Pro Gln
1               5                   10                  15

```
Leu Pro Gly Ser Val Ser Glu Ser Leu Glu Ser Arg Ala Arg Met
             20                  25                  30

Gly Val Glu Ser Tyr Leu Pro Cys Pro Leu Leu Pro Ala Tyr His Arg
         35                  40                  45

Pro Gly Ala Ser Gly Glu Ala Ser Ala Gly Asn Gly Thr Pro Arg Thr
     50                  55                  60

Thr Ala Thr Ala Thr Thr Thr Thr Ala Ser Pro Leu Arg Glu Gly Phe
65                  70                  75                  80

Gly Gly Gln Asp Gly Gly Glu Leu Trp Pro Leu Gln Ser Glu Gly Ala
                 85                  90                  95

Ala Ala Leu Val Thr Lys Glu Cys Gln Arg Leu Ala Ala Gln Gly Ala
            100                 105                 110

Arg Pro Glu Ala Pro Lys Arg Lys Trp Ala Lys Asp Gly Gly Asp Ala
            115                 120                 125

Pro Ser Pro Ser Lys Arg Pro Trp Ala Arg Gln Glu Asn Gln Glu Ala
            130                 135                 140

Lys Gly Glu Ser Gly Met Gly Cys Asp Ser Gly Ala Ser Asn Ser Ser
145                 150                 155                 160

Ser Ser Ser Ser Asn Thr Thr Ser Ser Ser Gly Glu Ala Ser Ala Arg
                165                 170                 175

Leu Arg Glu Glu Val Gln Pro Ser Ala Pro Glu Arg Leu Ala Leu Asp
            180                 185                 190

Tyr Ile Val Pro Cys Met Arg Tyr Tyr Gly Ile Cys Val Lys Asp Asn
            195                 200                 205

Phe Leu Gly Ala Val Leu Gly Gly Arg Val Leu Ala Glu Val Glu Ala
            210                 215                 220

Leu Lys Trp Gly Gly Arg Leu Arg Asp Gly Gln Leu Val Ser Gln Arg
225                 230                 235                 240

Ala Ile Pro Pro Arg Ser Ile Arg Gly Asp Gln Ile Ala Trp Val Glu
            245                 250                 255

Gly His Glu Pro Gly Cys Arg Ser Ile Gly Ala Leu Met Ala His Val
            260                 265                 270

Asp Ala Val Ile Arg His Cys Ala Gly Arg Leu Gly Asn Tyr Val Ile
            275                 280                 285

Asn Gly Arg Thr Lys Ala Met Val Ala Cys Tyr Pro Gly Asn Gly Leu
            290                 295                 300

Gly Tyr Val Arg His Val Asp Asn Pro His Gly Asp Gly Arg Cys Ile
305                 310                 315                 320

Thr Cys Ile Tyr Tyr Leu Asn Gln Asn Trp Asp Val Lys Val His Gly
                325                 330                 335

Gly Leu Leu Gln Ile Phe Pro Glu Gly Arg Pro Val Val Ala Asn Ile
            340                 345                 350

Glu Pro Leu Phe Asp Arg Leu Leu Ile Phe Trp Ser Asp Arg Arg Asn
            355                 360                 365

Pro His Glu Val Lys Pro Ala Tyr Ala Thr Arg Tyr Ala Ile Thr Val
            370                 375                 380

Trp Tyr Phe Asp Ala Lys Glu Arg Ala Ala Arg Asp Lys Tyr Gln
385                 390                 395                 400

Leu Ala Ser Gly Gln Lys Gly Val Gln Val Pro Val Ser Gln Pro Thr
            405                 410                 415

Thr Pro Thr
```

<210> SEQ ID NO 5
<211> LENGTH: 55
<212> TYPE: DNA
<213> ORGANISM: Artificial
<220> FEATURE:
<223> OTHER INFORMATION: Short hairpin sequence against PHD1

<400> SEQUENCE: 5
caccgctgca tcacctgtat ctatttctct tgaaaataga tacaggtgat gcagc       55

<210> SEQ ID NO 6
<211> LENGTH: 55
<212> TYPE: DNA
<213> ORGANISM: Artificial
<220> FEATURE:
<223> OTHER INFORMATION: Short hairpin sequence to knockdown PHD1
      expression

<400> SEQUENCE: 6
caccgctgca tcacctgtat ctatttctct tgaaaataga tacaggtgat gcagc       55

<210> SEQ ID NO 7
<211> LENGTH: 55
<212> TYPE: DNA
<213> ORGANISM: Artificial
<220> FEATURE:
<223> OTHER INFORMATION: Short hairpin sequence control

<400> SEQUENCE: 7
caccgcttaa cccgtattgc ctatttctct tgaaaatagg caatacgggt taagc       55

<210> SEQ ID NO 8
<211> LENGTH: 55
<212> TYPE: DNA
<213> ORGANISM: Homo sapiens

<400> SEQUENCE: 8
caccgctgca tcacctgtat ctatttctct tgaaaataga tacaggtgat gcagc       55

<210> SEQ ID NO 9
<211> LENGTH: 55
<212> TYPE: DNA
<213> ORGANISM: Homo sapiens

<400> SEQUENCE: 9
caccgccaac atcgagccac tcttttctct tgaaaagag tggctcgatg ttggc        55

<210> SEQ ID NO 10
<211> LENGTH: 23
<212> TYPE: DNA
<213> ORGANISM: Artificial
<220> FEATURE:
<223> OTHER INFORMATION: Forward primer PHD1

<400> SEQUENCE: 10
ggtacgtgag gcatgttgac aat                                          23

<210> SEQ ID NO 11
<211> LENGTH: 27
<212> TYPE: DNA
<213> ORGANISM: Artificial
<220> FEATURE:
<223> OTHER INFORMATION: Reverse primer PHD1

<400> SEQUENCE: 11
cttaacatcc cagttctgat tcaggta                                      27

```
<210> SEQ ID NO 12
<211> LENGTH: 18
<212> TYPE: DNA
<213> ORGANISM: Artificial
<220> FEATURE:
<223> OTHER INFORMATION: probe PHD1

<400> SEQUENCE: 12
cccacggcga tgggcgct                                                 18

<210> SEQ ID NO 13
<211> LENGTH: 24
<212> TYPE: DNA
<213> ORGANISM: Artificial
<220> FEATURE:
<223> OTHER INFORMATION: Forward primer PHD2

<400> SEQUENCE: 13
agtcccatga agtgatcaag ttca                                          24

<210> SEQ ID NO 14
<211> LENGTH: 19
<212> TYPE: DNA
<213> ORGANISM: Artificial
<220> FEATURE:
<223> OTHER INFORMATION: Reverse primer PHD2

<400> SEQUENCE: 14
atccgcatga tctgcatgg                                                19

<210> SEQ ID NO 15
<211> LENGTH: 25
<212> TYPE: DNA
<213> ORGANISM: Artificial
<220> FEATURE:
<223> OTHER INFORMATION: Probe PHD2

<400> SEQUENCE: 15
tgcccacgtc agagagcaac atcac                                         25

<210> SEQ ID NO 16
<211> LENGTH: 30
<212> TYPE: DNA
<213> ORGANISM: Artificial
<220> FEATURE:
<223> OTHER INFORMATION: Forward primer PHD3

<400> SEQUENCE: 16
ttatcagact gaagagctac tgtaatgatc                                    30

<210> SEQ ID NO 17
<211> LENGTH: 30
<212> TYPE: DNA
<213> ORGANISM: Artificial
<220> FEATURE:
<223> OTHER INFORMATION: Reverse primer PHD3

<400> SEQUENCE: 17
ttaccagtgt caattatatc ttcaacaatc                                    30

<210> SEQ ID NO 18
<211> LENGTH: 34
<212> TYPE: DNA
<213> ORGANISM: Artificial
<220> FEATURE:
```

<223> OTHER INFORMATION: Probe PHD3

<400> SEQUENCE: 18
tgagagatca tctccaccaa taactttatg tccc                         34

<210> SEQ ID NO 19
<211> LENGTH: 21
<212> TYPE: DNA
<213> ORGANISM: Artificial
<220> FEATURE:
<223> OTHER INFORMATION: Forward primer Glut1

<400> SEQUENCE: 19
gggcatgtgc ttccagtatg t                                       21

<210> SEQ ID NO 20
<211> LENGTH: 20
<212> TYPE: DNA
<213> ORGANISM: Artificial
<220> FEATURE:
<223> OTHER INFORMATION: Reverse primer Glut1

<400> SEQUENCE: 20
acgaggagca ccgtgaagat                                         20

<210> SEQ ID NO 21
<211> LENGTH: 24
<212> TYPE: DNA
<213> ORGANISM: Artificial
<220> FEATURE:
<223> OTHER INFORMATION: Probe Glut1

<400> SEQUENCE: 21
caactgtgcg gcccctacgt cttc                                    24

<210> SEQ ID NO 22
<211> LENGTH: 19
<212> TYPE: DNA
<213> ORGANISM: Artificial
<220> FEATURE:
<223> OTHER INFORMATION: Forward primer Glut4

<400> SEQUENCE: 22
gatctgccgc tccgaaaag                                          19

<210> SEQ ID NO 23
<211> LENGTH: 20
<212> TYPE: DNA
<213> ORGANISM: Artificial
<220> FEATURE:
<223> OTHER INFORMATION: Reverse primer Glut4

<400> SEQUENCE: 23
ggaagtctct cccacggtga                                         20

<210> SEQ ID NO 24
<211> LENGTH: 25
<212> TYPE: DNA
<213> ORGANISM: Artificial
<220> FEATURE:
<223> OTHER INFORMATION: Probe Glut4

<400> SEQUENCE: 24
taccaagcct cccagccctt acgct                                   25

-continued

<210> SEQ ID NO 25
<211> LENGTH: 20
<212> TYPE: DNA
<213> ORGANISM: Artificial
<220> FEATURE:
<223> OTHER INFORMATION: Forward primer alfa-actin

<400> SEQUENCE: 25
agagggaaat cgtgcgtgac                                              20

<210> SEQ ID NO 26
<211> LENGTH: 21
<212> TYPE: DNA
<213> ORGANISM: Artificial
<220> FEATURE:
<223> OTHER INFORMATION: Reverse primer alfa-actin

<400> SEQUENCE: 26
caatagtgat gacctggccg t                                            21

<210> SEQ ID NO 27
<211> LENGTH: 23
<212> TYPE: DNA
<213> ORGANISM: Artificial
<220> FEATURE:
<223> OTHER INFORMATION: Probe alfa-actin

<400> SEQUENCE: 27
cactgccgca tcctcttcct ccc                                          23

<210> SEQ ID NO 28
<211> LENGTH: 17
<212> TYPE: DNA
<213> ORGANISM: Artificial
<220> FEATURE:
<223> OTHER INFORMATION: LNA directed to murine PHD1 Sequence

<400> SEQUENCE: 28
aggctgaggg aggaagt                                                 17

<210> SEQ ID NO 29
<211> LENGTH: 21
<212> TYPE: DNA
<213> ORGANISM: Artificial
<220> FEATURE:
<223> OTHER INFORMATION: PHD1 shRNA target sequence

<400> SEQUENCE: 29
gctgcatcac ctgtatctat t                                            21

<210> SEQ ID NO 30
<211> LENGTH: 21
<212> TYPE: DNA
<213> ORGANISM: Artificial
<220> FEATURE:
<223> OTHER INFORMATION: PHD1 shRNA target sequence

<400> SEQUENCE: 30
gccaacatcg agccactctt t                                            21

<210> SEQ ID NO 31

```
-continued

<211> LENGTH: 21
<212> TYPE: DNA
<213> ORGANISM: Artificial
<220> FEATURE:
<223> OTHER INFORMATION: PHD1 shRNA target sequence

<400> SEQUENCE: 31
ggtgttcaag taccagtatc a                                              21
```